(12) United States Patent
Eisinger

(10) Patent No.: US 11,534,172 B2
(45) Date of Patent: Dec. 27, 2022

(54) ELECTROMECHANICAL SURGICAL STAPLER INCLUDING TROCAR ASSEMBLY RELEASE MECHANISM

(71) Applicant: Covidien LP, Mansfield, MA (US)

(72) Inventor: Joseph Eisinger, Northford, CT (US)

(73) Assignee: COVIDIEN LP, Mansfield, MA (US)

( * ) Notice: Subject to any disclaimer, the term of this patent is extended or adjusted under 35 U.S.C. 154(b) by 339 days.

(21) Appl. No.: 16/829,128

(22) Filed: Mar. 25, 2020

(65) Prior Publication Data

US 2020/0222050 A1 Jul. 16, 2020

Related U.S. Application Data

(63) Continuation-in-part of application No. 15/972,606, filed on May 7, 2018, now Pat. No. 10,932,784.

(60) Provisional application No. 62/836,905, filed on Apr. 22, 2019.

(51) Int. Cl.
*A61B 17/115* (2006.01)
*A61B 17/34* (2006.01)
*A61B 17/00* (2006.01)

(52) U.S. Cl.
CPC ...... *A61B 17/1155* (2013.01); *A61B 17/3476* (2013.01); *A61B 2017/00486* (2013.01)

(58) Field of Classification Search
CPC ........... A61B 2017/07271; A61B 2017/00734; A61B 2017/00486; A61B 2017/00411; A61B 17/1155

See application file for complete search history.

(56) References Cited

U.S. PATENT DOCUMENTS

| 2,957,353 A | 10/1960 | Babacz |
| 3,111,328 A | 11/1963 | Di Rito et al. |
| 3,695,058 A | 10/1972 | Keith, Jr. |

(Continued)

FOREIGN PATENT DOCUMENTS

| CA | 2451558 A1 | 1/2003 |
| CN | 1547454 A | 11/2004 |

(Continued)

OTHER PUBLICATIONS

Extended European Search Report dated Sep. 22, 2020 corresponding to counterpart Patent Application EP 20170561.3.

(Continued)

*Primary Examiner* — Joshua G Kotis
*Assistant Examiner* — Scott A Howell

(57) ABSTRACT

An adapter assembly for connecting a surgical reload to an electromechanical handle assembly, includes a trocar assembly release mechanism configured to releasably secure the trocar assembly within an outer tube. The release mechanism includes a release button supported in the outer tube and movable between an extended condition and a depressed condition; a spring clip slidably supported in the outer tube and connected to the release button; and a pair of lock cam pins supported within the outer tube, wherein each lock cam pin is secured to a respective leg of the spring clip, and wherein each lock cam pin is selectively receivable within a respective opening of the pair of openings formed in the trocar housing. The spring clip includes a backspan connected to the release button; and a pair of legs extending from the backspan.

22 Claims, 30 Drawing Sheets

(56) References Cited

U.S. PATENT DOCUMENTS

| | | |
|---|---|---|
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,567,047 A * | 10/1996 | Fritsch .................. A47J 43/082 403/325 |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |

(56) References Cited

U.S. PATENT DOCUMENTS

| | | | |
|---|---|---|---|
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,136,712 B2 * | 3/2012 | Zingman | A61B 17/1155 227/175.3 |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 * | 8/2014 | Ross | A61B 17/072 74/89.32 |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,392,910 B2 * | 7/2016 | Brenna | A47J 43/082 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |

(56) References Cited

U.S. PATENT DOCUMENTS

| | | |
|---|---|---|
| 2005/0116009 A1* | 6/2005 | Milliman ............ A61B 17/1155 227/176.1 |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0284792 A1* | 10/2013 | Ma ...................... A61B 90/30 227/176.1 |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0310134 A1 | 10/2016 | Contini et al. |
| 2016/0361057 A1* | 12/2016 | Williams ............ A61B 17/068 |

(56) References Cited

U.S. PATENT DOCUMENTS

| | | | |
|---|---|---|---|
| 2017/0333077 A1 | 11/2017 | Williams et al. | |
| 2018/0280024 A1 | 10/2018 | Williams | |
| 2018/0360460 A1 | 12/2018 | Mozdzierz et al. | |
| 2020/0188053 A1 | 6/2020 | Williams et al. | |
| 2020/0222050 A1* | 7/2020 | Eisinger | A61B 17/3476 |
| 2020/0222051 A1* | 7/2020 | Eisinger | A61B 17/1155 |
| 2021/0204952 A1* | 7/2021 | Sgroi | A61B 17/34 |

FOREIGN PATENT DOCUMENTS

| | | | |
|---|---|---|---|
| CN | 1957854 | A | 5/2007 |
| CN | 101495046 | A | 7/2009 |
| CN | 101856251 | A | 10/2010 |
| CN | 102247182 | A | 11/2011 |
| DE | 102008053842 | A1 | 5/2010 |
| EP | 0705571 | A1 | 4/1996 |
| EP | 1563793 | A1 | 8/2005 |
| EP | 1759652 | A2 | 3/2007 |
| EP | 1769754 | A1 | 4/2007 |
| EP | 1908412 | A2 | 4/2008 |
| EP | 1917929 | A1 | 5/2008 |
| EP | 1952769 | A2 | 8/2008 |
| EP | 2090247 | A1 | 8/2009 |
| EP | 2245994 | A1 | 11/2010 |
| EP | 2316345 | A1 | 5/2011 |
| EP | 2377472 | A1 | 10/2011 |
| EP | 2668910 | A2 | 12/2013 |
| EP | 2815705 | A1 | 12/2014 |
| ES | 2333509 | A1 | 2/2010 |
| FR | 2861574 | A1 | 5/2005 |
| JP | 2005125075 | A | 5/2005 |
| KR | 20120022521 | A | 3/2012 |
| WO | 2011108840 | A2 | 9/2011 |
| WO | 2012/040984 | A1 | 4/2012 |

OTHER PUBLICATIONS

Extended European Search Report corresponding to International Application No. EP 14 18 4882.0 dated May 12, 2015.
Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Notification of Transmittal of the International Search Report and The Written Opinion of the International Searching Authority issued in corresponding application No. PCT/US2016/027042 dated Jul. 12, 2016.

* cited by examiner

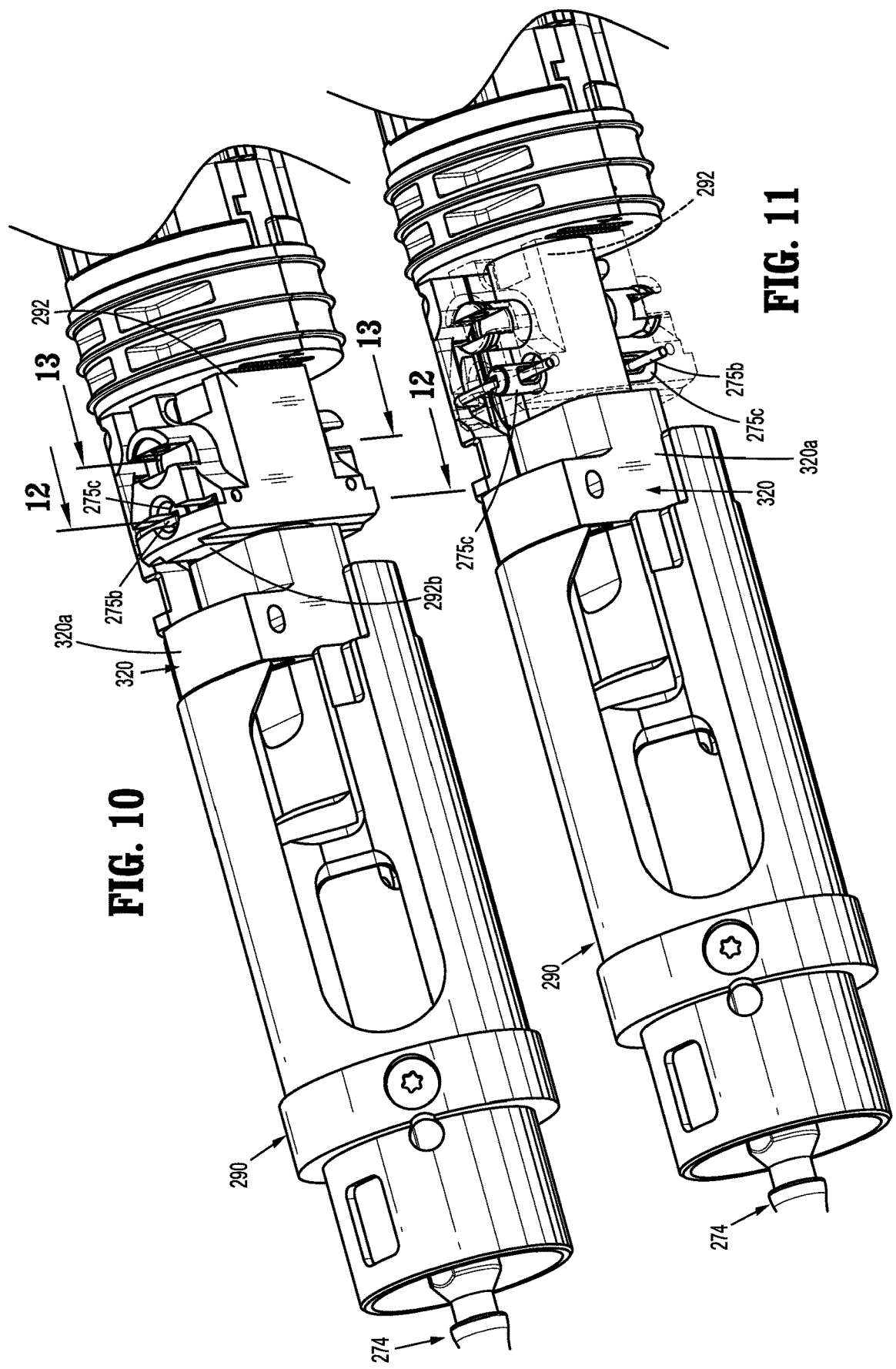

ELECTROMECHANICAL SURGICAL STAPLER INCLUDING TROCAR ASSEMBLY RELEASE MECHANISM

CROSS-REFERENCE TO RELATED APPLICATIONS

The present application claims the benefit of and priority to U.S. Provisional Patent Application Ser. No. 62/836,905, filed on Apr. 22, 2019, the entire content of which being hereby incorporated by reference.

The present application is also a Continuation-in-Part Application which claims the benefit of and priority to U.S. patent application Ser. No. 15/972,606, filed on May 7, 2018, the entire content of which being hereby incorporated by reference.

BACKGROUND

1. Technical Field

The present disclosure relates to powered surgical devices. More specifically, the present disclosure relates to reusable handheld electromechanical surgical devices including trocar assembly release mechanisms or trocar lock assemblies, and trocar connection indicators.

2. Background of Related Art

Circular stapling instruments for performing surgical procedures such as anastomoses, hemorrhoidectomies, and mucosectomies are well known. These devices include an anvil assembly having a center rod and an anvil head supported on the center rod. The center rod of the anvil assembly is attachable to a trocar of the circular stapling instrument which enables linear translation of the anvil assembly. Typically, during a surgical procedure, the tool assembly of the circular stapling instrument is inserted into a tubular section or sections of tissue to join the tissue sections or remove diseased or damaged tissue from within the tissue section. Following a surgical procedure, it is desirable to reprocess the circular stapling instrument in order to minimize overall costs of the surgical procedures. The reprocessing typically requires cleaning of the circular stapling instrument via autoclaving and the like. In order to improve the efficiency of the reprocessing, removability of the trocar is desirable.

Accordingly, in view thereof, it is desirable to provide locks and indicators which alert the end user (e.g., doctor, nurse, clinician, etc.) that a trocar is properly attached to the underlying circular stapling instrument.

SUMMARY

In accordance with aspects of the present disclosure, an adapter assembly includes an outer tube, a trocar assembly, and a trocar release mechanism. The trocar assembly is disposed within a distal portion of the outer tube. The trocar release mechanism includes a pair of pins, a release button, a spring clip, and a spring latch. The pair of pins is slidably supported within the outer tube. The release button is supported in the outer tube and is movable between an extended condition and a depressed condition. The spring clip is slidably supported in the outer tube. The spring clip interconnects the release button and the pair of pins such that when the release button is in the extended condition, the trocar assembly is secured to the outer tube and when the release button is in the depressed condition, the trocar assembly is removable from the outer tube. The spring latch is fixed to the release button such that the spring clip is secured to the release button.

In aspects, the trocar release mechanism includes a pair of pins that are slidably supported within the outer tube. The spring clip may interconnect the release button with the pair of pins. In the extended condition of the release button, the spring clip may maintain the pair of pins in an extended position and in the depressed condition of the release button, the spring clip may withdraw the pair of pins form the extended position to a withdrawn position.

In some aspects, the trocar assembly includes a trocar housing and a trocar that is slidably disposed within the trocar housing. The trocar housing may define a pair of radially opposed openings. Each pin of the trocar release mechanism may be received within a respective opening of the pair of openings to secure the trocar assembly within the outer tube in the extended position and withdrawn from the respective opening in the withdrawn position. In the extended position the pair of pins is configured to provide a visual indication to a user that the trocar assembly is locked in the outer tube.

In certain aspects, the outer tube defines a pair of opposed openings. The pair of pins of the trocar release mechanism has a fully extended position in which each pin extends into a respective one of the opposed openings in which the pair of pins are configured to provide a visual indication to a user that the trocar assembly is not secured within the outer tube. The trocar release mechanism may include a biasing member that is supported within the outer tube and acts on the release button to urge the release button to the extended condition.

In particular aspects, the spring latch may include a planar body and a pair of staking tabs that extends orthogonally from the planar body into an inner surface of the release button to fix the spring latch to the release button. The spring clip may be movable in two degrees of freedom when secured to the release button by the spring latch.

In some aspects, the spring clip includes a backspan that is secured to the release button by the spring latch and a pair of legs that extend from the back span. Each leg may include a gooseneck portion along a length thereof such that a distal portion of each pair of legs is closer to one another as compared to a proximal portion of each of the pair of legs. Movement of the release button between the extended condition and the depressed condition moves the gooseneck portion of each of the pair of legs of the spring clip to traverse the pair of pins. When the release button is in the extended condition, the distal portion of each of the spring clap may be associated with a respective pin and when the release button is in the depressed condition, the proximal portion of each leg of the spring clip may be associated with the respective pin.

In certain aspects, the adapter assembly is configured to releasably secure to an electromechanical handle assembly.

A method of manufacturing an adapter assembly includes fixing a spring latch to an inner surface of a release button, disposing the release button within a space defined in an outer tube of the adapter assembly, and providing a trocar assembly that is configured to be disposed within the outer tube and is secured within the outer tube by a spring clip that is secured to the release button by the spring latch. Fixing the spring latch to the inner surface of the release button may include aligning the body of the spring latch with the inner surface of the release button, heating two staking tabs of the spring latch that extends orthogonally from a body of the spring latch, and driving the staking tabs into the inner surface of the release button to fix the spring latch to the release button.

In aspects, driving the staking tabs into the inner surface of the release button includes the staking tabs melting holes into the inner surface. The method may include positioning a backspan of the spring clip within a groove defined in the inner surface of the release button before fixing the spring latch to the inner surface. Aligning the body of the spring latch with the inner surface of the release button may include positioning a retention tab that extends form the body over a portion of the backspan of the spring clip disposed within the groove.

In some aspects, the method includes positioning a backspan of the spring clip within a groove defined in the inner surface of the release button after fixing the spring latch to the inner surface of the release button.

In certain aspects the method includes cutting a flat sheet of metal to form the body, the staking tabs, and a retention tab of the spring latch such that the staking tabs extend from opposite sides of the body and the retention tab extends from a side of the body positioned between the opposite sides of the body. The method may include aligning the staking tabs downward such that the staking tabs are positioned orthogonal to a plane defined by the body. The method may also include bending the retention tab upward to a goose neck configuration such that an inner surface of the retention tab is arcuate towards a center of curvature that is disposed in a plane defined by the body.

In another aspect of the present disclosure, an adapter assembly for connecting a surgical reload to an electromechanical handle assembly is provided. The adapter assembly includes: an outer tube; a trocar assembly releasably securable within a distal end of the outer tube, the trocar assembly including a trocar housing defining a pair of openings therein, wherein the pair of openings are in opposed radially extending relation to one another; and a trocar assembly release mechanism configured to releasably secure the trocar assembly within the outer tube.

The release mechanism includes: a pair of pins slidably supported within the outer tube, wherein each pin is selectively receivable within a respective opening of the pair of openings formed in the trocar housing; a release button supported in the outer tube and movable between an extended condition and a depressed condition; and a spring clip slidably supported in the outer tube, the spring clip interconnecting the release button and the pair of pins.

When the release button is in the extended condition, the spring clip acts on the pair of pins to maintain the pair of pins disposed within the pair of openings of the trocar housing to maintain the trocar assembly connected to the outer tube. When the release button is in the depressed condition, the spring clip acts on the pair of pins to maintain the pair of pins withdrawn from the pair of openings of the trocar housing to release the trocar assembly from the outer tube.

The pair of pins may be extended radially outwardly when the release button is in the depressed condition, whereby a visual indication is provided to a user that the trocar assembly is not locked in the outer tube.

The trocar assembly release mechanism may further include a biasing member supported within the outer tube and acting on the release button to urge the release button to the extended condition.

The spring clip of the trocar assembly release mechanism may include a backspan connected to the release button, and a pair of legs extending from the backspan. Each leg may define a gooseneck along a length thereof such that a distal portion of each of the pair of legs is closer to one another as compared to a proximal portion of each of the pair of legs.

Movement of the release button between the extended condition and the depressed condition may cause the gooseneck portion of the pair of legs of the spring clip to traverse the pair of pins.

When the release button is in the extended condition, the distal portions of the pair of legs of the spring clip may be associated with the pair of pins. When the release button is in the depressed condition, the proximal portions of the pair of legs of the spring clip may be associated with the pair of pins.

The trocar assembly may further include: a trocar member slidably disposed within a lumen of the trocar housing, wherein the trocar member and the trocar housing are keyed to one another to inhibit rotation relative to one another, wherein the trocar member includes a distal end defining a tip and a proximal end defining an internally threaded bore; and a drive screw having a threaded distal portion engaged with the threaded bore of the trocar member, and a proximal force receiving feature for receiving rotative forces from the electromechanical handle assembly.

The outer tube may include a pair of openings formed through an outer surface thereof. Each of the pair of openings of the outer tube may be in registration with a respective one of the pair of pins.

When the release button is in the depressed condition, the pair of pins may be at least partially disposed within the pair of openings of the outer tube.

According to another aspect of the present disclosure, an adapter assembly for connecting a surgical reload to an electromechanical handle assembly is provided. The adapter assembly includes: an outer tube; a trocar assembly releasably securable within a distal end of the outer tube, the trocar assembly including a trocar housing defining a pair of openings therein, wherein the pair of openings are in opposed radially extending relation to one another; and a trocar assembly release mechanism configured to releasably secure the trocar assembly within the outer tube.

The release mechanism includes: a pair of release buttons rotatably supported on opposed radial sides of the outer tube, wherein each release button is selectively receivable within a respective opening of the pair of openings formed in the trocar housing, each release button being movable between a release condition and an engaged condition; and a pair of biasing members supported in the outer tube and associated with a respective one of the pair of release buttons, wherein the biasing members urge the pair of release buttons to the engaged condition and into engagement with the trocar housing.

When the release buttons are in the engaged condition, the release buttons are disposed within the pair of openings of the trocar housing to maintain the trocar assembly connected to the outer tube. When the release buttons are in the depressed condition, the release buttons are disengaged from the pair of openings of the trocar housing to release the trocar assembly from the outer tube.

The trocar release mechanism may include a pair of pivot pins, each pivot pin pivotably supporting a respective release button.

Each release button may be substantially semi-circular, extending substantially 180° about a respective pivot pin thereof.

Each release button may define a distal face against which a portion of a respective biasing member engages to urge release button to the engaged condition and into engagement with the trocar housing.

Each release button may define a proximal face projecting to a tail, wherein the tails enter a respective opening of the pair of openings of the trocar housing, when the release buttons are in the engaged condition, to maintain the trocar assembly connected to the outer tube.

Each release button may include gripping features formed thereon.

According to a further aspect of the present disclosure, an adapter assembly for connecting a surgical reload to an electromechanical handle assembly, is provided. The adapter assembly includes an outer tube; a trocar assembly releasably securable within a distal end of the outer tube, the trocar assembly including a trocar housing defining a pair of openings therein, wherein the pair of openings are in opposed radially extending relation to one another; and a trocar assembly release mechanism configured to releasably secure the trocar assembly within the outer tube.

The release mechanism includes a pair of rocker pins rotatably supported within the outer tube, wherein each rocker pin is selectively receivable within a respective opening of the pair of openings formed in the trocar housing; a release button supported in the outer tube and movable between an extended condition and a depressed condition; and a spring clip slidably supported in the outer tube, the spring clip connected to the release button and received in a pocket of each of the pair of rocker pins.

When the release button is in the extended condition, the spring clip acts on the pair of rocker pins to maintain the pair of rocker pins disposed within the pair of openings of the trocar housing to maintain the trocar assembly connected to the outer tube. When the release button is in the depressed condition, the spring clip acts on the pair of rocker pins to maintain the pair of rocker pins withdrawn from the pair of openings of the trocar housing to release the trocar assembly from the outer tube.

The pair of rocker pins may be rotated radially outwardly when the release button is in the depressed condition.

The trocar assembly release mechanism may further include a biasing member supported within the outer tube and acting on the release button to urge the release button to the extended condition.

The spring clip of the trocar assembly release mechanism may include a backspan connected to the release button; and a pair of legs extending from the backspan, wherein each leg defines an inturned distal free end such that the distal free end of each of the pair of legs is closer to one another as compared to a proximal portion of each of the pair of legs.

Movement of the release button between the extended condition and the depressed condition may cause the distal free end of the pair of legs of the spring clip to rotate the pair of rocker pins, and may cause the pair of legs of the spring clip to splay radially outward.

When the release button is in the extended condition, the distal free end of each of the pair of legs of the spring clip may bias the pair of rocker pins radially towards one another.

The trocar assembly may further include a trocar member slidably disposed within a lumen of the trocar housing. The trocar member and the trocar housing may be keyed to one another to inhibit rotation relative to one another. The trocar member may include a distal end defining a tip and a proximal end defining an internally threaded bore.

The trocar assembly may further include a drive screw having a threaded distal portion engaged with the threaded bore of the trocar member, and a proximal force receiving feature for receiving rotative forces from the electromechanical handle assembly.

According to a further aspect of the present disclosure, an adapter assembly for connecting a surgical reload to a handle assembly, is provided. The adapter assembly includes an outer tube; a trocar assembly disposed within a distal portion of the outer tube; and a trocar release mechanism. The trocar release mechanism includes a pair of rocker pins rotatably supported within the outer tube, each rocker pin defining a pocket therein; a release button supported in the outer tube and movable between an extended condition and a depressed condition; and a spring clip slidably supported in the outer tube, the spring clip connected to the release button and received in each pocket of the pair of rocker pins such that when the release button is in the extended condition the trocar assembly is secured to the outer tube and when the release button is in the depressed condition the trocar assembly is removable from the outer tube.

In the extended condition of the release button, the spring clip may maintain the pair of rocker pins in an extended position. In the depressed condition of the release button, the spring clip may withdraw the pair of rocker pins from the extended position to a withdrawn position.

The trocar assembly may include a trocar housing and a trocar slidably disposed within the trocar housing.

The trocar housing may define a pair of radially opposed openings. Each rocker pin of the trocar release mechanism may be received within a respective opening of the pair of openings to secure the trocar assembly within the outer tube in the extended position and withdrawn from the respective opening in the withdrawn position.

The trocar release mechanism may further include a biasing member supported within the outer tube and acting on the release button to urge the release button to the extended condition.

The spring clip may include a backspan pivotally secured to the release button; and a pair of legs extending from the backspan, wherein each leg defines an inturned distal free end such that the distal free end of each of the pair of legs is closer to one another as compared to a proximal end of each of the pair of legs.

Movement of the release button between the extended condition and the depressed condition may move the pair of legs of the spring clip to rotate the pair of rocker pins.

According to still another aspect of the present disclosure, a further adapter assembly for connecting a surgical reload to an electromechanical handle assembly, is provided. The adapter assembly includes an outer tube; a trocar assembly releasably securable within a distal end of the outer tube, the trocar assembly including a trocar housing defining a pair of openings therein, wherein the pair of openings are in opposed radially extending relation to one another; and a trocar assembly release mechanism configured to releasably secure the trocar assembly within the outer tube. The release mechanism includes a release button supported in the outer tube and movable between an extended condition and a depressed condition; and a spring clip slidably supported in the outer tube and connected to the release button. The spring clip includes a backspan connected to the release button; and a pair of legs extending from the backspan. The release mechanism further includes a pair of lock cam pins supported within the outer tube, wherein each lock cam pin is secured to a respective leg of the spring clip, and wherein each lock cam pin is selectively receivable within a respective opening of the pair of openings formed in the trocar housing. Wherein, when the release button is moved from the extended condition to the depressed condition, the spring clip acts on the pair of lock cam pins to withdraw the pair of lock cam pins from the openings of the trocar housing to release the trocar assembly from the outer tube.

When the release button is moved from the depressed condition to the extended condition, the spring clip may act on the pair of lock cam pins to urge the pair of lock cam pins into the openings of the trocar housing to lock the trocar assembly into the outer tube.

The trocar assembly release mechanism may further include a biasing member supported within the outer tube and acting on the release button to urge the release button to the extended condition.

The spring clip of the trocar assembly release mechanism may create a spring bias when the release button is moved from the extended condition to the depressed condition.

Movement of the release button from the extended condition to the depressed condition may cause the pair of legs of the spring clip to splay outwardly.

When the release button is in the extended condition, the pair of legs of the spring clip may bias the pair of lock cam pins towards one another.

Each lock cam pin may include a lock boss extending from a respective leg of the spring clip; and a cam surface configured for engagement by a feature of the adapter assembly to cause the lock cam pin to move outwardly as the release button from the extended condition to the depressed condition.

Each lock boss may be configured for receipt into the openings of the trocar housing to lock the trocar assembly into the outer tube.

The adapter assembly may further include a pair of camming surfaces respectively associated with the cam surface of each of the lock cam pins.

When the release button is moved from the extended condition to the depressed condition, the cam surfaces of the lock cam pins may engage respective camming surfaces of the adapter assembly to withdraw the pair of lock cam pins from the openings of the trocar housing to release the trocar assembly from the outer tube.

During movement of the release button from the extended condition to the depressed condition, the pair of legs of the spring clip may be splayed outwardly, whereby a spring bias is created in the spring clip.

The spring bias of the spring clip may urge the pair of legs towards one another to move the pair of lock cam pins towards one another.

The spring bias of the spring clip may urge the release button from the depressed condition to the extended condition.

The trocar assembly may further include a trocar member slidably disposed within a lumen of the trocar housing, wherein the trocar member and the trocar housing are keyed to one another to inhibit rotation relative to one another, wherein the trocar member includes a distal end defining a tip and a proximal end defining an internally threaded bore; and a drive screw having a threaded distal portion engaged with the threaded bore of the trocar member, and a proximal force receiving feature for receiving rotative forces from the electromechanical handle assembly.

BRIEF DESCRIPTION OF THE DRAWINGS

Embodiments of the present disclosure are described herein with reference to the accompanying drawings, wherein:

FIG. 10 is a perspective view, of a distal end portion of the first force/rotation transmitting/converting assembly of FIG. 7, illustrating a support block thereof, and a trocar lock assembly associated therewith;

FIG. 11 is a perspective view, of a distal end portion of the first force/rotation transmitting/converting assembly of FIG. 7, with the support block thereof shown in phantom;

DETAILED DESCRIPTION OF EMBODIMENTS

Figure 1:
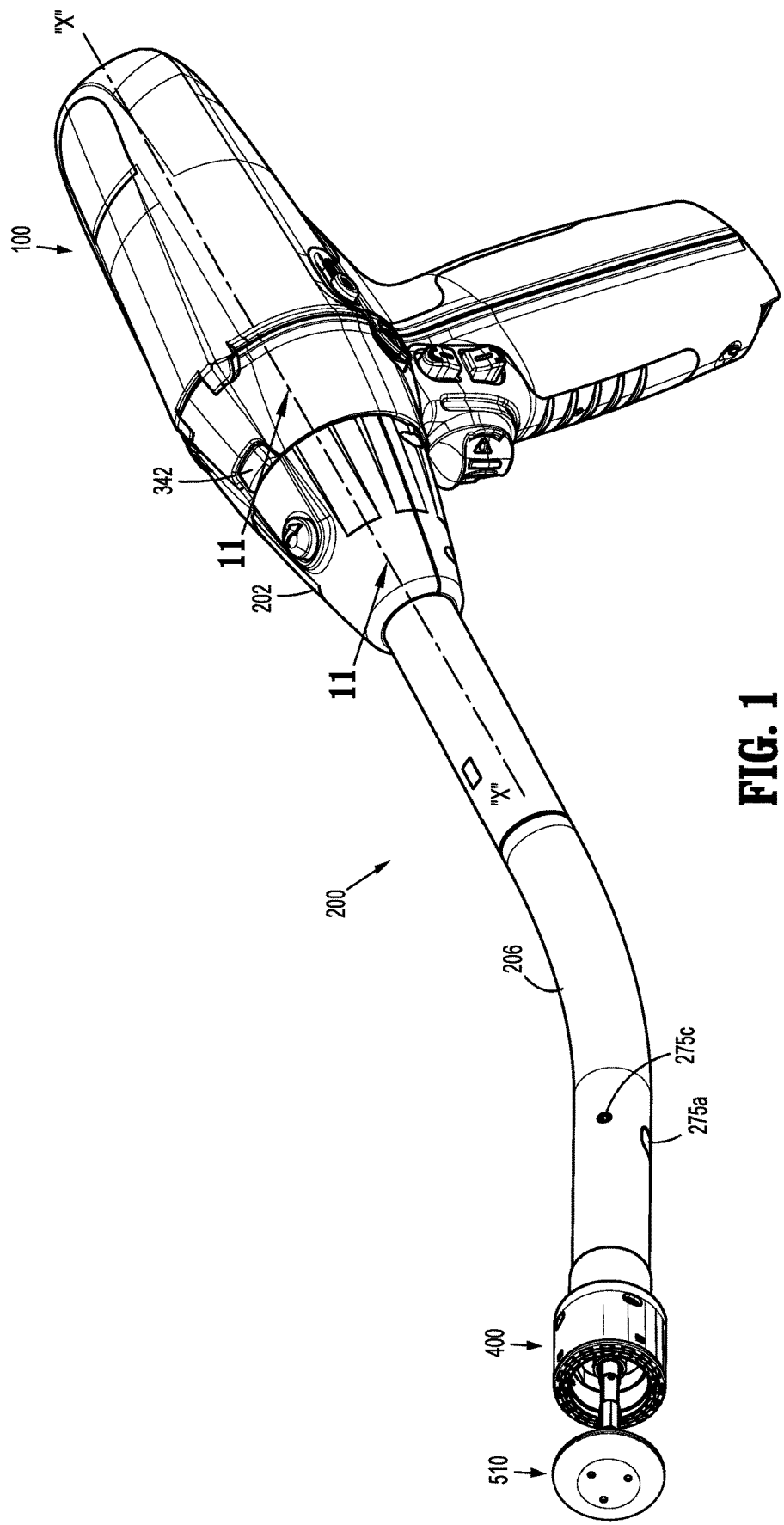
FIG. 1 is a perspective view of a handheld surgical device including a handle assembly, an adapter assembly, and a reload in accordance with an embodiment of the present disclosure.

Embodiments of the present disclosure are now described in detail with reference to the drawings, in which like reference numerals designate identical or corresponding elements in each of the several views. As used herein the term "proximal" refers to a portion of a surgical device, or component thereof, closer to the user, and the term "distal" refers to a portion of the surgical device, or component thereof, farther from the user.

Turning now to FIG. 1, a surgical device 10, in accordance with an embodiment of the present disclosure, is in the form of a powered handheld electromechanical instrument. The surgical device includes a handle assembly 100, an adapter assembly 200, a reload 400, and an anvil assembly 510. The handle assembly 100 is configured for selective connection with the adapter assembly 200 and, in turn, the adapter assembly 200 is configured for selective connection with the reload 400.

The handle assembly 100, the adapter assembly 200, and the reload 400 will only further be described to the extent necessary to disclose aspects of the present disclosure. For a detailed description of the structure and function of exemplary handle assemblies, adapter assemblies, and reloads, reference may be made to commonly owned U.S. Patent Application Publication No. 2016/0310134 and U.S. patent application Ser. No. 15/972,606, the entire content of each of which is incorporated herein by reference.

Figure 2:
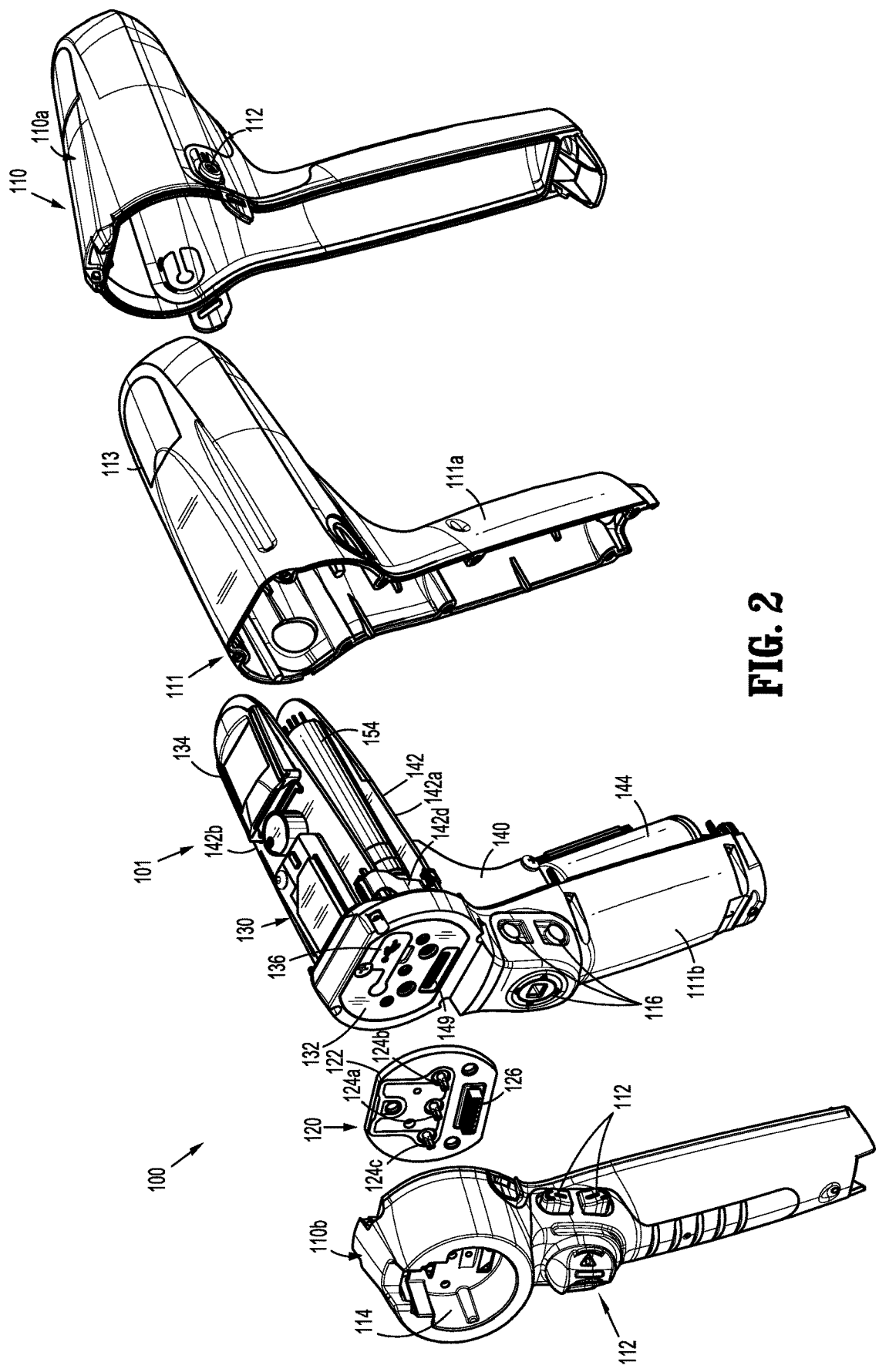
FIG. 2 is a perspective view, with parts separated, of the handle assembly of FIG. 1.

With reference now to FIG. 2, the handle assembly 100 includes a power handle 101 and an outer or shell housing 110 configured to selectively receive and encase the power handle 101. The shell housing 110 includes a proximal half-section 110a and a distal half-section 110b that are couplable together. The shell housing 110 includes a plurality of actuators 112 (e.g., finger-actuated control buttons, knobs, toggles, slides, interfaces, and the like) for activating various functions of the surgical device 10 (FIG. 1) upon application of a respective force thereto.

The distal half-section 110b of the shell housing 110 defines a connecting portion 114 (e.g., a recess) configured to accept or receive a corresponding drive coupling assembly 210 (FIG. 5) of the adapter assembly 200. A sterile barrier plate assembly 120 is selectively supported in the distal half-section 110b of the shell housing 110 behind the connection portion 114. The plate assembly 120 includes a plate 122 rotatably supporting three coupling shafts 124a, 124b, 124c, and having an electrical connector 126 supported thereon. The electrical connector 126 includes a chip and defines a plurality of contact paths each including an electrical conduit for extending an electrical connection across the plate 122. When the plate assembly 120 is disposed within the shell housing 110, distal ends of the coupling shafts 124a, 124b, 124c and the electrical connector 126 are disposed or situated within the connecting portion 114 of the shell housing 110 to electrically and/or mechanically engage respective corresponding features of the adapter assembly 200, as will be described in greater detail below.

The power handle 101 has an inner handle housing 111 including a proximal half section 111a and a distal half section 111b that are coupled together to house a power-pack core assembly 130 therein. The power-pack core assembly 130 is configured to control the various operations of the handle assembly 100 and thus, the surgical device 10.

The distal half section 111b of the inner handle housing 111 is configured and adapted to support a control plate 132 of the power-pack core assembly 130 such that the control plate 132 abuts the plate assembly 120 of the shell housing 110 when the power handle 101 is disposed within the shell housing 110. The distal half section 111b of the inner handle housing 111 also supports a plurality of actuator interfaces 116 that are in operative registration with the respective actuators 112 of the shell housing 110.

Figure 3:
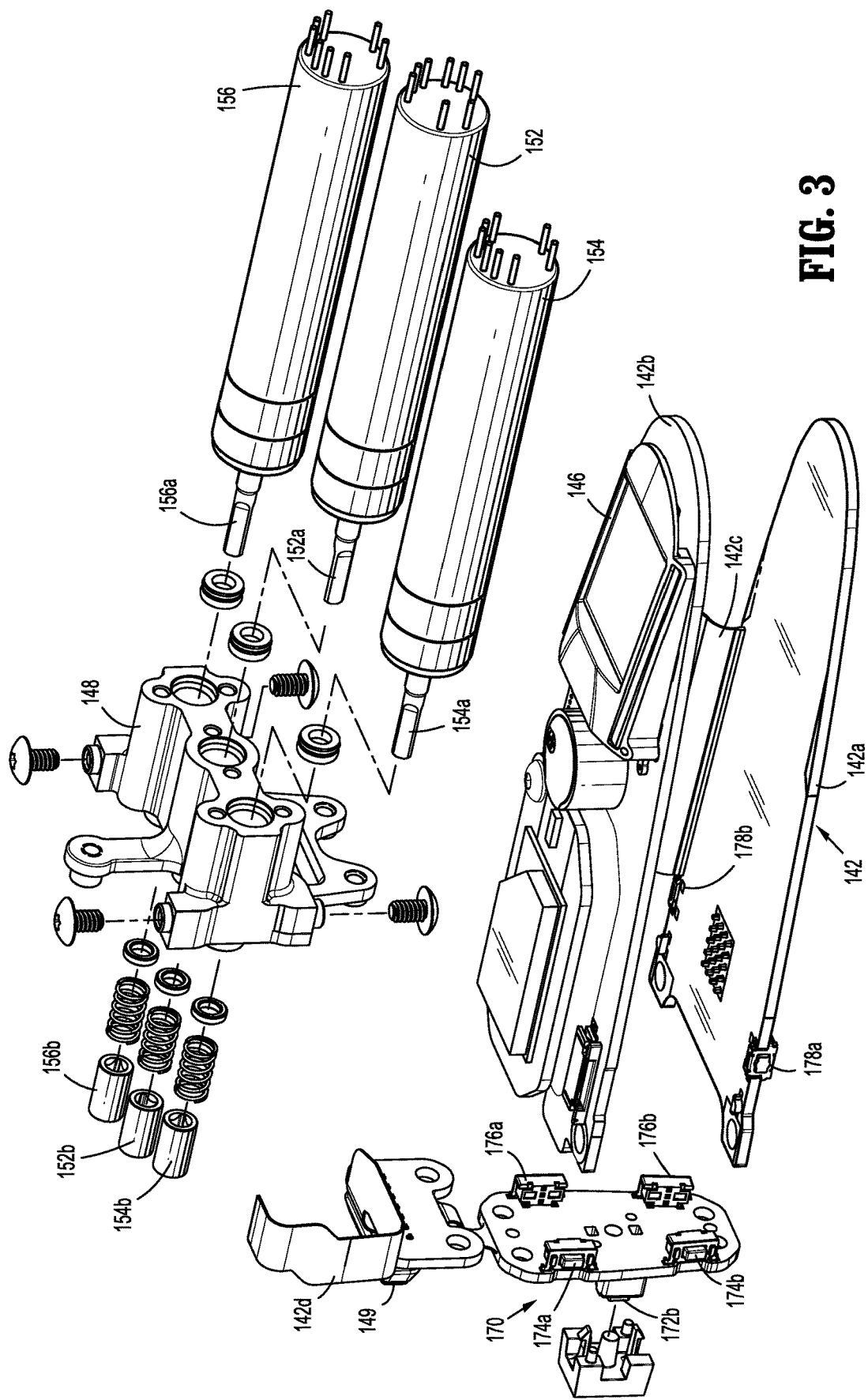
FIG. 3 is a perspective view, with parts separated, of a motor assembly and a control assembly of a power handle of the handle assembly of FIG. 2.

As shown in FIGS. 2 and 3, the power-pack core assembly 130 includes a battery circuit 140, a controller circuit board 142, and a rechargeable battery 144 configured to supply power to any of the electrical components of the handle assembly 100. The controller circuit board 142 includes a motor controller circuit board 142a, a main controller circuit board 142b, and a first ribbon cable 142c interconnecting the motor controller circuit board 142a and the main controller circuit board 142b. A display screen 134 is supported on the main controller circuit board 142b and visible through a clear or transparent window 113 provided in the proximal half-section 111a of the inner handle housing 111. A USB connector 136 (or other data connector) is also supported on the main controller circuit board 142b and is accessible through the control plate 132 of the power-pack core assembly 130.

The power-pack core assembly 130 further includes a first motor 152, a second motor 154, and a third motor 156 disposed between the motor controller circuit board 142a and the main controller circuit board 142b. Each of the first, second, and third motors 152, 154, 156 is electrically connected to the controller circuit board 142 and the battery 144, and controlled by a respective motor controller disposed on the motor controller circuit board 142a which, in turn, is coupled to a respective main controller disposed on the main controller circuit board 142b.

Each of the first, second, and third motors 152, 154, 156 is supported on a motor bracket 148 such that respective motor shaft 152a, 154a, 156a extending from the first, second, and third motors 152, 154, 156 are rotatably disposed within respective apertures of the motor bracket 148. The motor bracket 148 rotatably supports three rotatable drive connector sleeves 152b, 154b, 156b that are keyed to the respective motor shafts 152a, 154a, 156a of the first, second, and third motors 152, 154, 156. The drive connector sleeves 152b, 154b, 156b non-rotatably receive proximal ends of the respective coupling shafts 124a, 124b, 124c of the plate assembly 120 of the shell housing 110, when the power handle 101 is disposed within the shell housing 10, and are each spring biased away from the respective motors 152, 154, 156.

The motor bracket 148 also supports an electrical receptacle 149. The electrical receptacle 149 is in electrical connection with the main controller circuit board 142b by a second ribbon cable 142d. The electrical receptacle 149 defines a plurality of electrical slots for receiving respective electrical contacts or blades extending from the pass-through connector 126 of the plate assembly 120 of the shell housing 110.

Rotation of the motor shafts 152a, 154a, 156a by the respective first, second, and third motors 152, 154, 156 function to drive shafts and/or gear components of the adapter assembly 200 in order to perform the various operations of the handle assembly 100, as will be described in greater detail below.

In use, when the adapter assembly 200 is mated to the handle assembly 100, each of the coupling shafts 124a, 124b, 124c of the handle assembly 100 couples with a corresponding rotatable connector sleeve 218, 222, 220 (FIG. 6) of the adapter assembly 200. In this regard, the interface between corresponding coupling shafts 124a, 124b, 124c and connector sleeves 218, 222, 220 are keyed such that rotation of each of the coupling shafts 124a, 124b, 124c of the handle assembly 100 causes a corresponding rotation of the corresponding connector sleeve 218, 222, 220 of the adapter assembly 200.

The coupling shafts 124a, 124b, 124c of handle assembly 100 are configured to be independently rotated by the respective motor 152, 154, 156 such that rotational force(s) are selectively transferred from the motors 152, 154, 156 of the handle assembly 100 to the adapter assembly 200. The selective rotation of the coupling shaft(s) 124a, 124b, 124c of the handle assembly 100 allows the handle assembly 100 to selectively actuate different functions of the reload 400.

Figure 4:
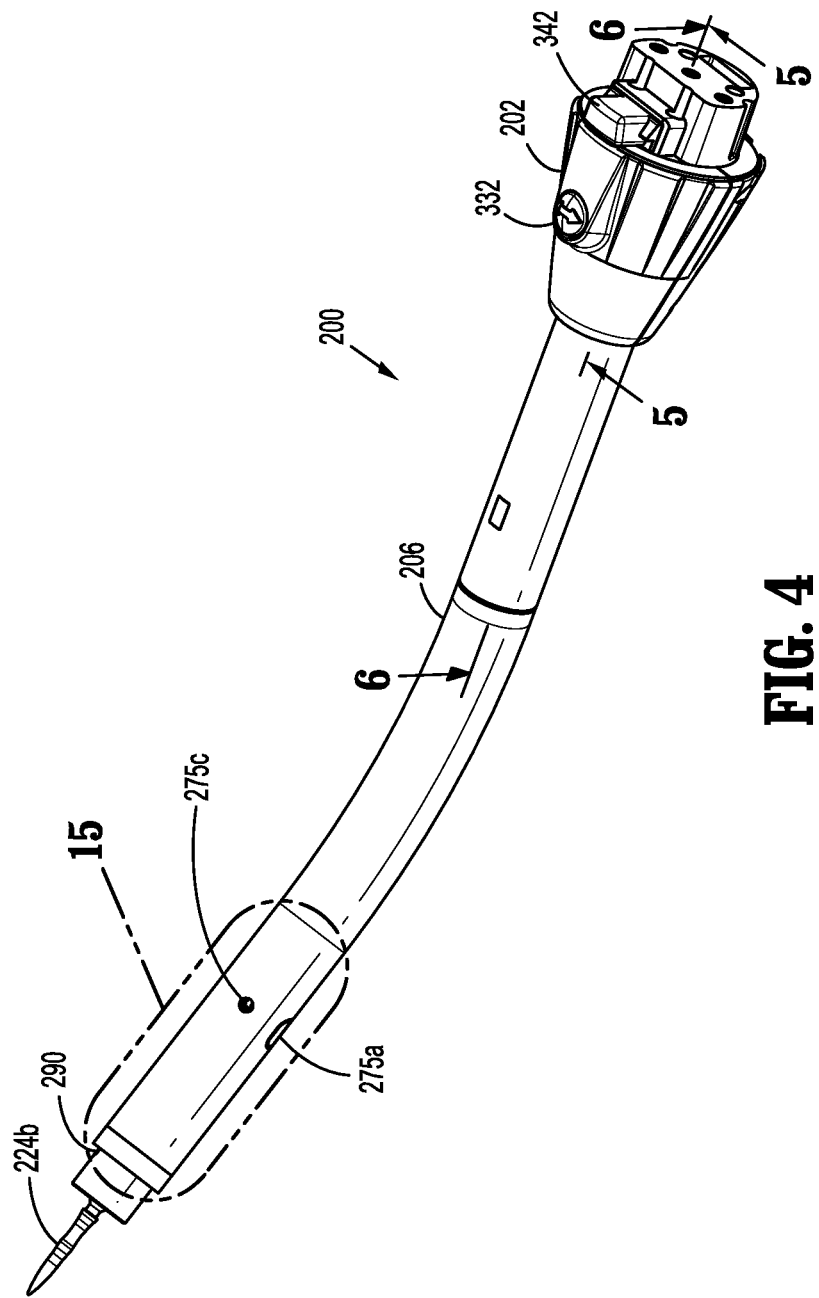
FIG. 4 is a perspective view of the adapter assembly without the reload secured to a distal end thereof.

Turning now to FIG. 4, the adapter assembly 200 is configured to convert a rotation of the coupling shaft(s) 124a, 124b, 124c (FIG. 2) of the handle assembly 100 into axial translation useful for effecting various functions of the surgical device 10 (FIG. 1). The adapter assembly 200 includes an adapter or knob housing 202 and an outer tube 206 extending from a distal end of the knob housing 202. The knob housing 202 and the outer tube 206 are configured and dimensioned to house and support the components of the adapter assembly 200. The knob housing 202 includes a drive coupling assembly 210 which is configured and adapted to connect to the connecting portion 114 (FIG. 2) of the shell housing 110 of the handle assembly 100. The outer tube 206 includes a connector sleeve 290 fixedly supported at a distal end thereof. The connector sleeve 290 is configured to selectively secure the reload 400 (FIG. 1) to the adapter assembly 200.

Figure 5:
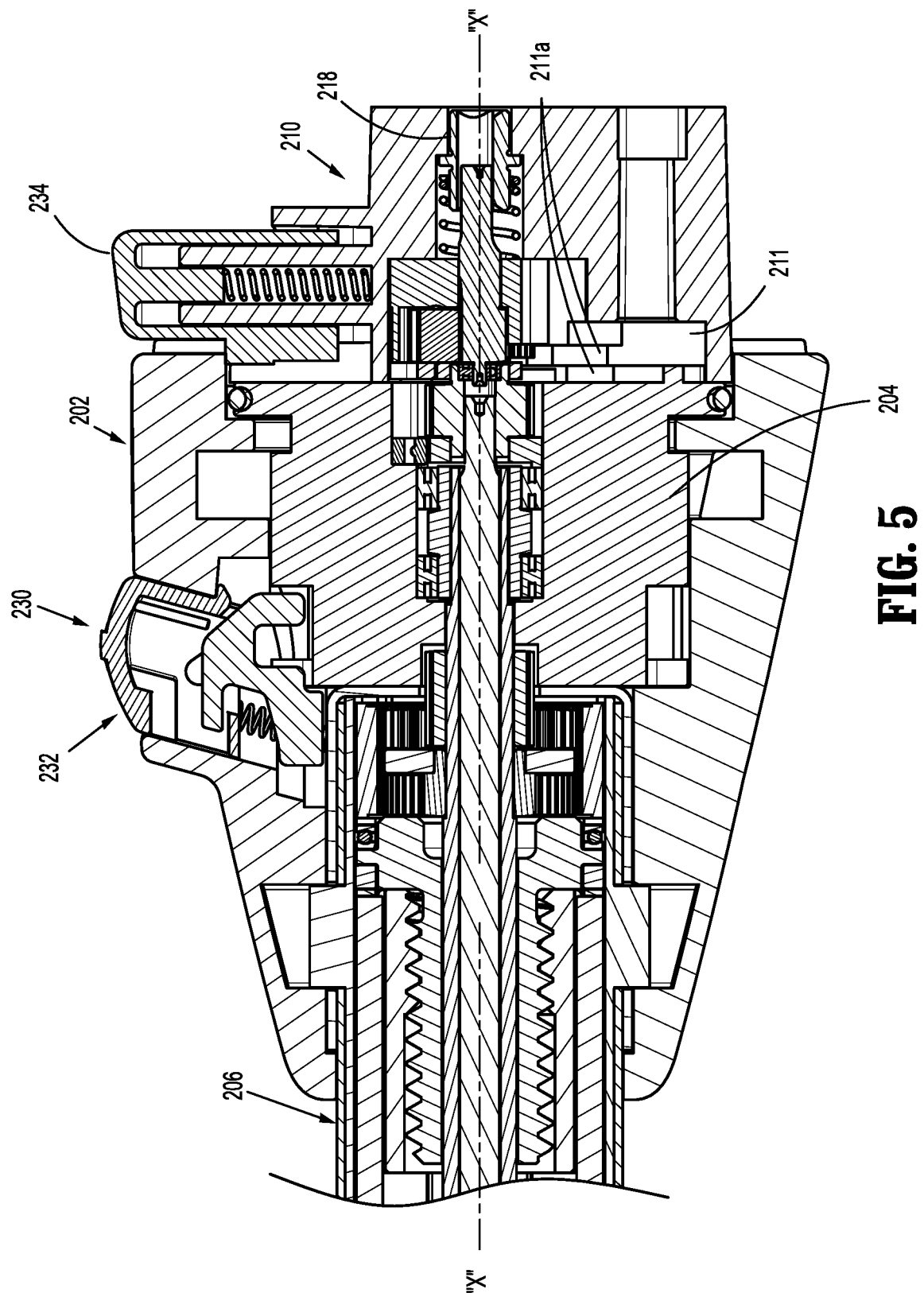
FIG. 5 is a cross-sectional view of the adapter assembly of FIG. 4, as taken through section line 5-5 of FIG. 4.

As shown in FIGS. 4 and 5, the adapter assembly 200 includes a rotation assembly 230 configured to enable rotation of the adapter assembly 200 relative to the handle assembly 100. Specifically, the knob housing 202 and the outer tube 206 of the adapter assembly 200 are rotatable relative to the drive coupling assembly 210 of the adapter assembly 200. The rotation assembly 230 includes a lock button 232 operably supported on the knob housing 202 and configured for actuating the rotation assembly 230. When rotation assembly 230 is in an unlocked configuration, the knob housing 202 and the outer tube 206 are rotatable along a longitudinal axis "X" of the adapter assembly 200 relative to the drive coupling assembly 210. When rotation assembly 230 is in a locked configuration, the knob housing 202 and the outer tube 206 are rotationally secured relative to the drive coupling assembly 210.

The adapter assembly 200 further includes an attachment/detachment button 234 supported on the drive coupling assembly 210 of the adapter assembly 200. In use, when the adapter assembly 200 is connected to the shell housing 110 of the handle assembly 100, the attachment/detachment button 234 secures and retains the adapter assembly 200 and the handle assembly 100 with one another. When the attachment/detachment button 234 is depressed or actuated, the adapter assembly 200 and the handle assembly 100 may be disconnected from each other.

Figure 22:
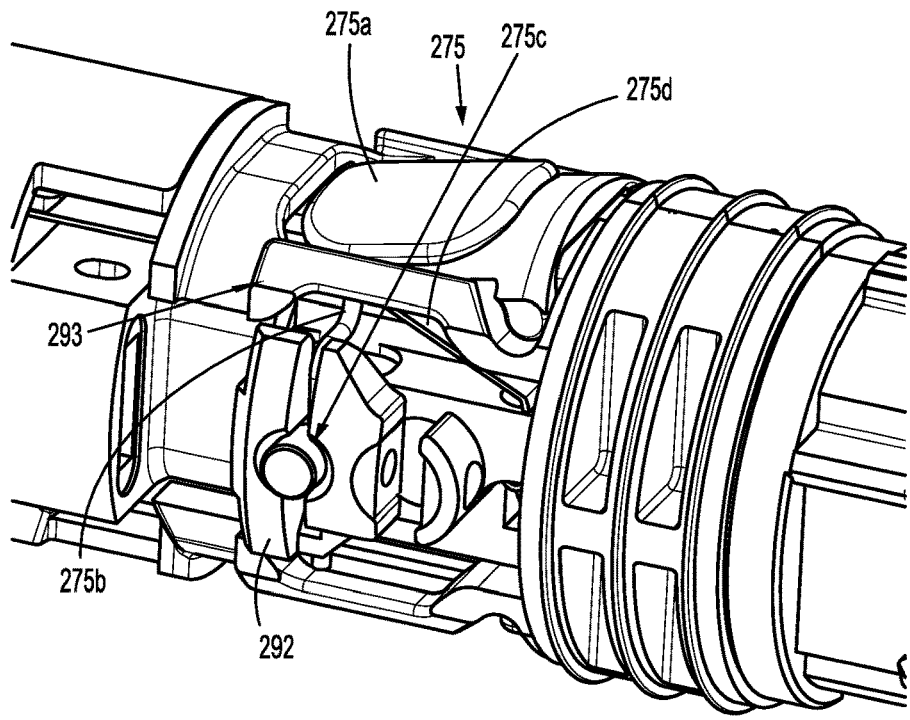
FIG. 22 is a perspective view, of a distal end portion of the first force/rotation transmitting/converting assembly of FIG. 7, illustrating the trocar lock assembly associated therewith in a depressed condition.

The adapter assembly 200 further includes a cavity 211 defined within the drive coupling assembly 210 that is configured to receive a pin connector assembly 320 (FIG. 22) of an electrical assembly 300 configured for establishing an electrical connection with and between the handle assembly 100, the adapter assembly 200, and the reload 400, as described in further detail below. The cavity 211 may include guiding ribs 211 configured to receive a printed circuit board 324 of the pin connector assembly 320.

Figure 6:
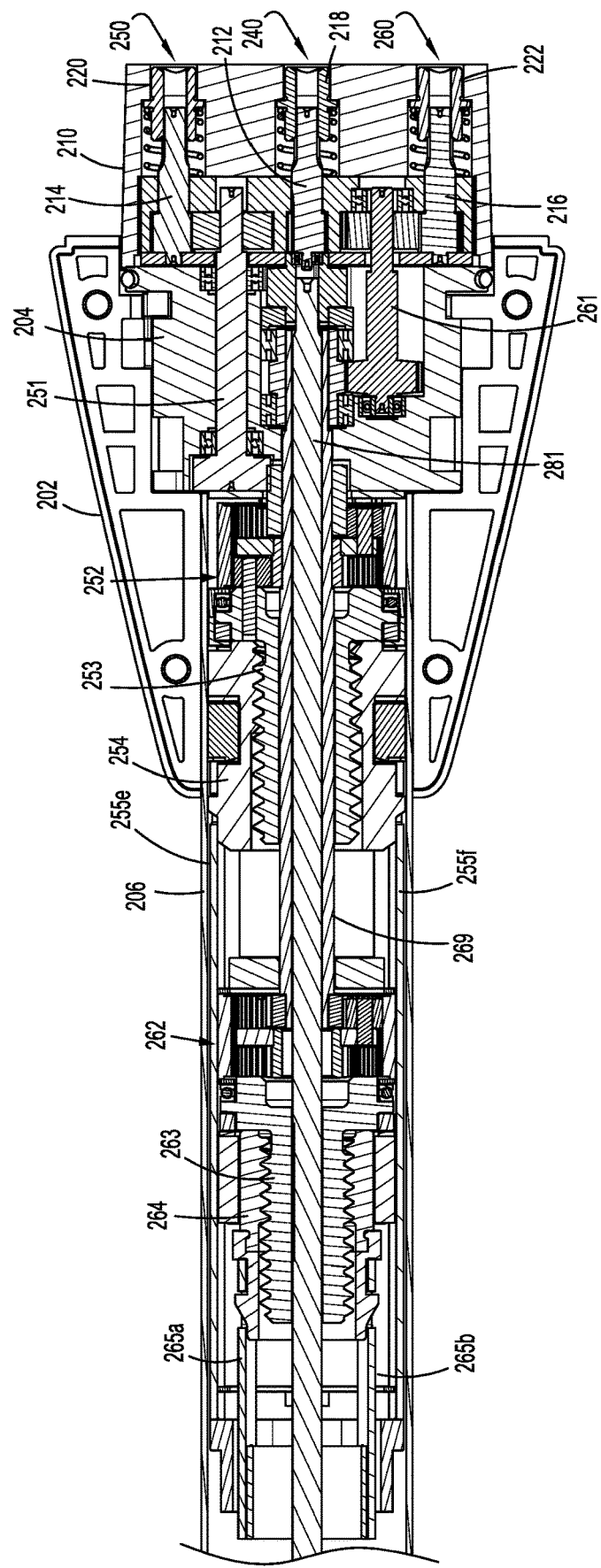
FIG. 6 is a cross-sectional view of the adapter assembly of FIG. 4, as taken through section line 6-6 of FIG. 4.

As illustrated in FIG. 6, the drive coupling assembly 210 of the adapter assembly 200 rotatably supports first, second, and third connector sleeves 218, 220 and 222 therein, and an inner housing member 204 disposed within the knob housing 202 rotatably supports first, second, and third rotatable proximal drive shafts 212, 214, 216 therein. Each of the first, second, and third connector sleeves 218, 220, 222 is configured to mate with a respective coupling shaft 124a, 124c, 124b (FIG. 2) of the handle assembly 100. Each of the first, second, and third connector sleeves 218, 220, 222 is further configured to mate with a proximal end of the respective first, second, and third proximal drive shafts 212, 214, 216 of the adapter assembly 200 such that each of the first, second, and third proximal drive shafts 212, 214, 216 functions as a rotation receiving member to receive rotational forces from the respective coupling shafts 124a, 124c, 124b of the handle assembly 100.

The adapter assembly 200 includes first, second and third force/rotation transmitting/converting assemblies 240, 250, 260 disposed within the inner housing member 204 and the outer tube 206. Each of the force/rotation transmitting/converting assemblies 240, 250, 260 is configured and adapted to transmit or convert a rotation of the respective coupling shaft 124a, 124c, 124b of the handle assembly 100 into axial translation to effectuate operation of the reload 400 (FIG. 1), as will be described in greater detail below.

Figure 7:
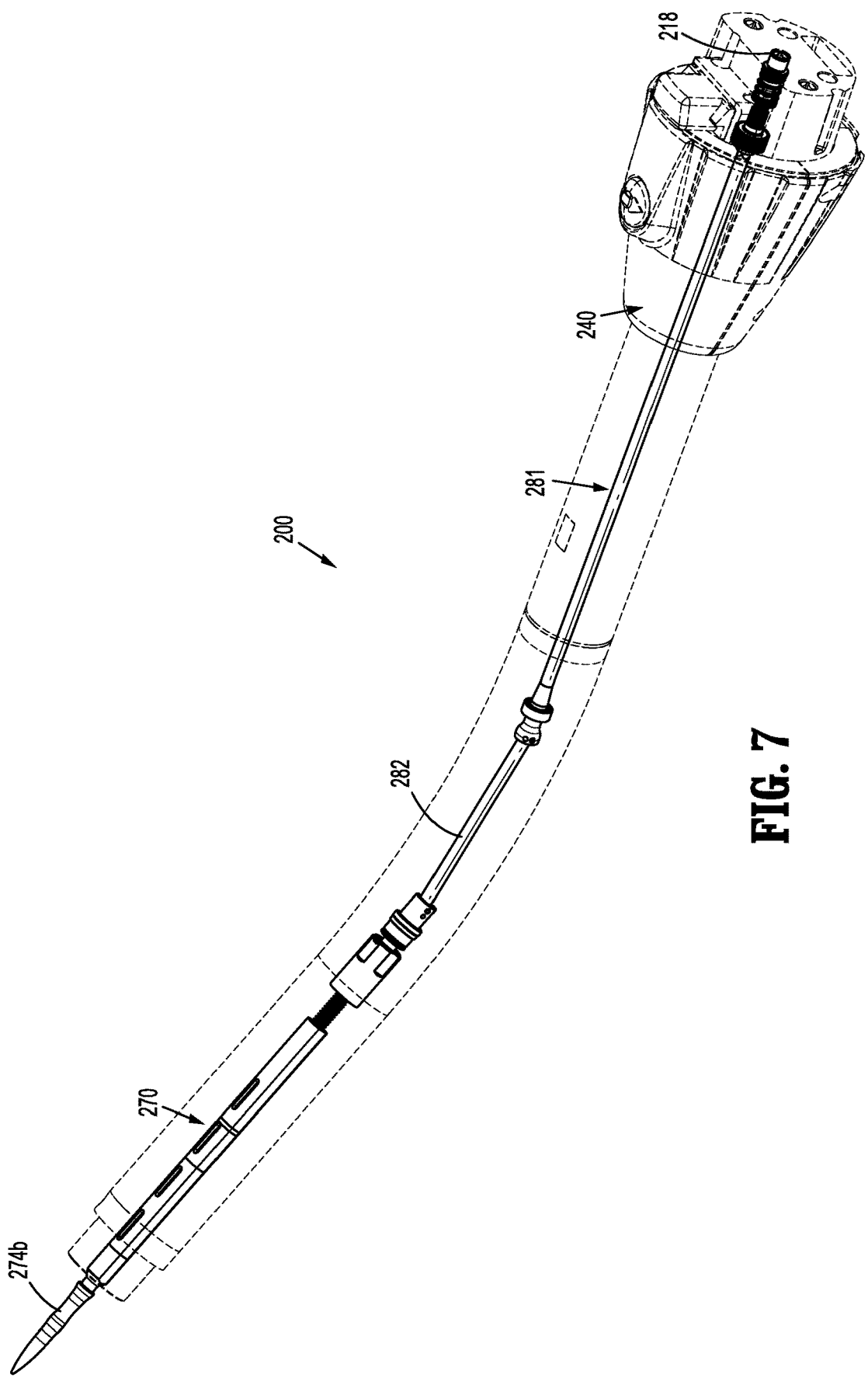
FIG. 7 is a perspective view of the adapter assembly, shown partially in phantom, illustrating a first force/rotation transmitting/converting assembly thereof.

As shown in FIGS. 6 and 7, the first force/rotation transmitting/converting assembly 240 includes the first rotatable proximal drive shaft 212, as described above, a second rotatable proximal drive shaft 281, a rotatable distal drive shaft 282, and a coupling member 286. First force/rotation transmitting/converting assembly 240, as illustrated in FIGS. 7-17, further includes a trocar assembly 270 removably supported in a distal end of outer tube 206. Trocar assembly 270 includes a tubular outer housing 272, a trocar member 274 slidably disposed within tubular outer housing 272, and a drive screw 276 operably received within trocar member 274 for axially moving trocar member 274 relative to tubular housing 272. In particular, trocar member 274 includes a proximal end 274a having an inner threaded portion 273 which engages a threaded distal portion 276b of drive screw 276. Trocar member 274 further includes at least one longitudinally extending flat 274d formed in an outer surface thereof which mates with a corresponding flat 272b formed in tubular housing 272 thereby inhibiting rotation of trocar member 274 relative to tubular housing 272 as drive screw 276 is rotated. A distal end 274b of trocar member 274 is configured to selectively engage anvil assembly 510 (FIG. 1).

Tubular housing 272 of trocar assembly 270 is axially and rotationally fixed within outer tube 206 of adapter assembly 200. Tubular housing 272 defines a pair of radially opposed, and radially oriented openings 272a which are configured and dimensioned to cooperate with a pair of lock pins 275c of a trocar assembly release mechanism or trocar lock assembly 275 (see FIGS. 10-14 and 17) of adapter assembly 200. With continued reference to FIGS. 10-17, adapter assembly 200 includes a support block 292 fixedly disposed within outer tube 206. The pair of lock pins 275c extend through support block 292 and into tubular housing 272 of trocar assembly 270 to connect trocar assembly 270 to adapter assembly 200.

Figure 23:
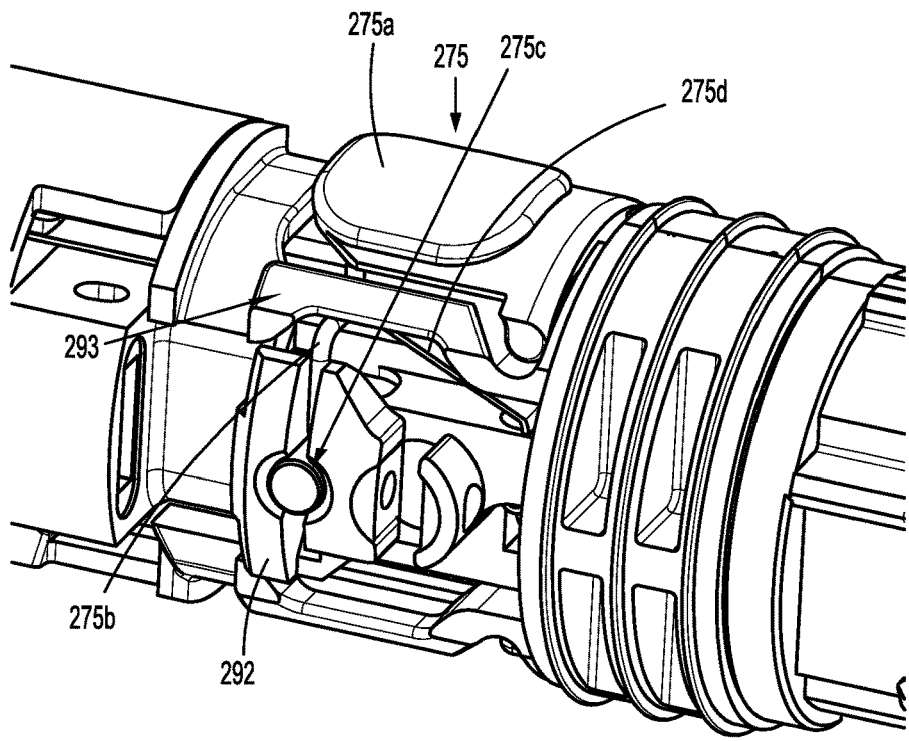
FIG. 23 is a perspective view, of a distal end portion of the first force/rotation transmitting/converting assembly of FIG. 7, illustrating the trocar lock assembly associated therewith in an undepressed condition.
Figure 24:
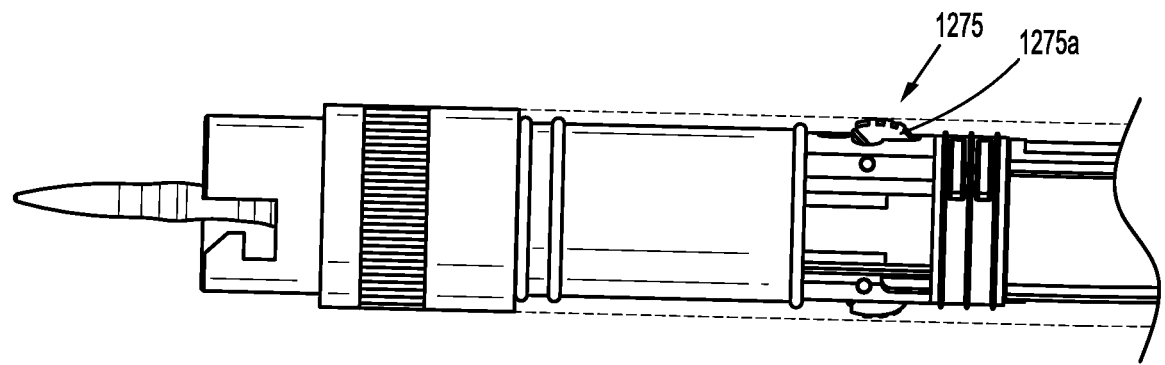
FIG. 24 is a perspective view of a distal end of an adapter assembly, without the reload secured to a distal end thereof, illustrating a trocar lock assembly according to another embodiment of the present disclosure.
Figure 25:
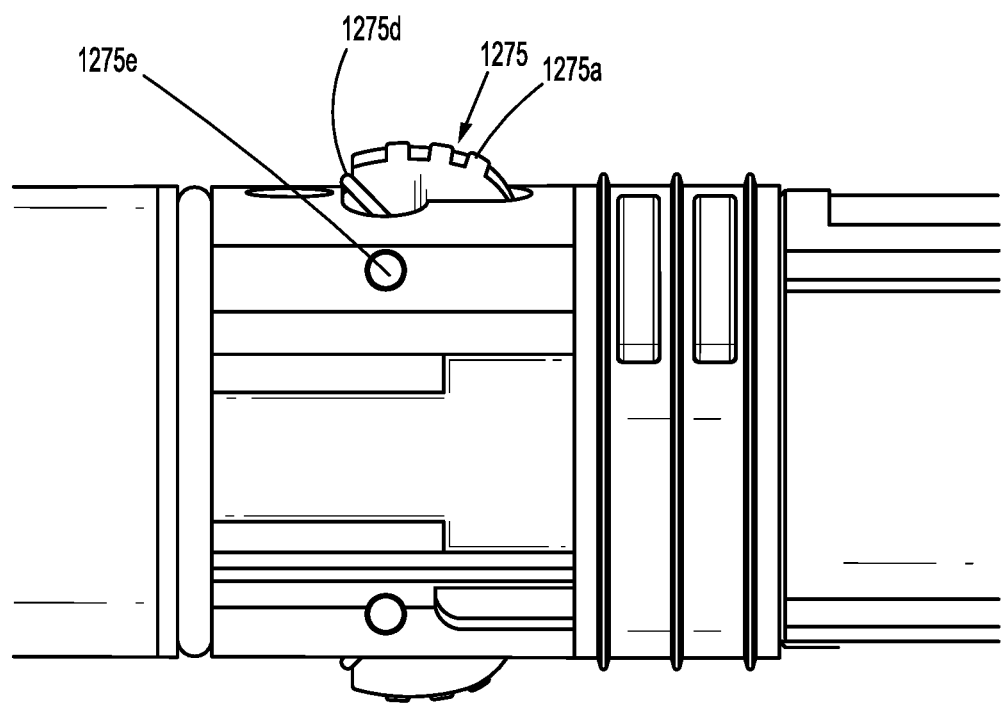
FIG. 25 is a top, plan view of the trocar lock assembly of FIG. 24, with an outer tube of the adapter assembly removed.
Figure 26:
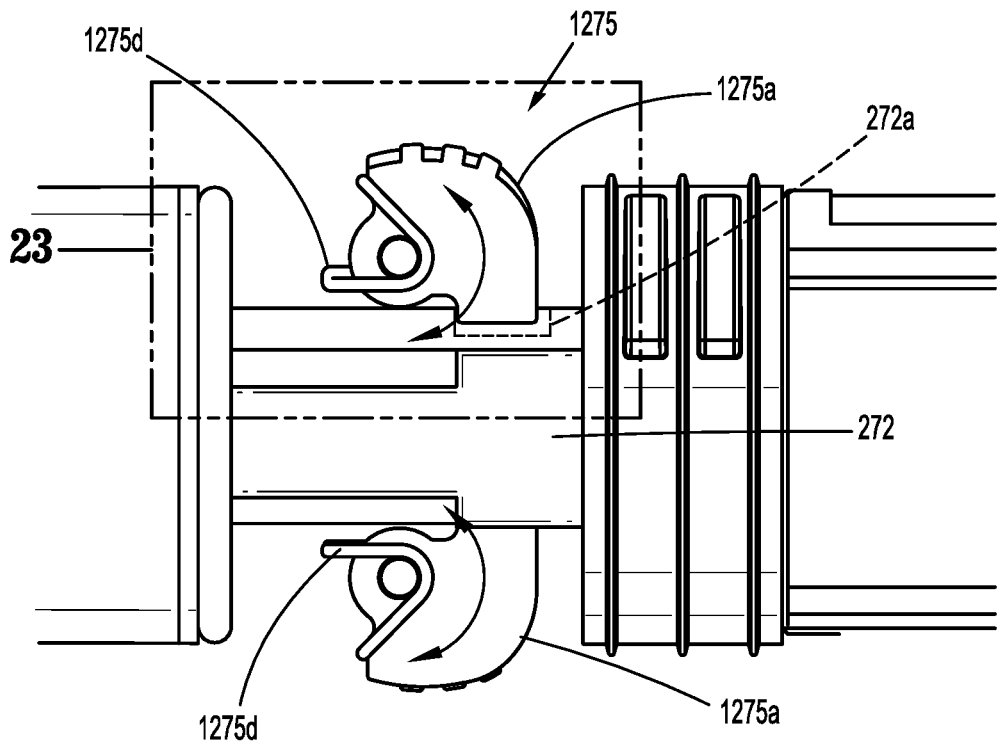
FIG. 26 is a top, plan view of the trocar lock assembly of FIG. 24, with an outer tube and a support block of the adapter assembly removed, illustrating the trocar lock assembly in a second locked position.

As illustrated in FIGS. 11-17, trocar assembly release mechanism 275 includes a release button 275a pivotally supported on a hinge guide 293 and in outer tube 206. Release button 275a is biased, via a spring 275d (see FIGS. 14, 22, and 23), to a locked/extended condition. Trocar assembly release mechanism 275 further includes a spring clip 275b having a backspan 1285b connected to release button 275a, and a pair of legs 1285a, extending from the backspan 1285b, that extend through support block 292 and transversely across trocar assembly 270. Each of the pair of legs 1285a of spring clip 275b extends through a respective lock pin 275c which is slidably disposed within a respective radial opening 272a of tubular housing 272 and radial opening 292a of support block 292. Each of the pair of legs 1285a of spring clip 275b defines a gooseneck along a length thereof such that a distal portion of each of the pair of legs 1285a of spring clip 275b is closer to one another as compared to a proximal portion of each of the pair of legs 1285a of spring clip 275b.

Figure 18:
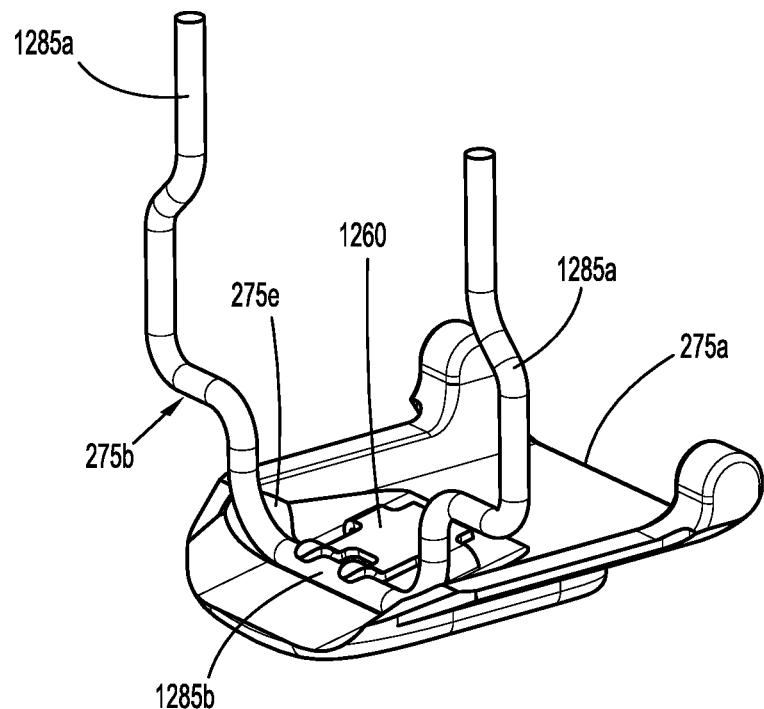
FIG. 18 is a perspective view of a release button and a spring clip of FIG. 17 with a spring latch securing the spring clip to an inner surface of the release button.
Figure 19:
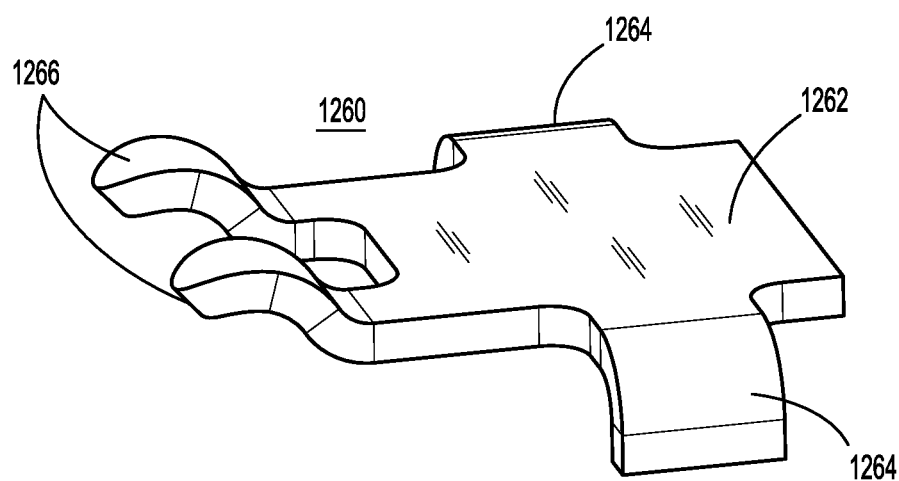
FIG. 19 is a perspective view of the spring latch of FIG. 18.
Figure 20:
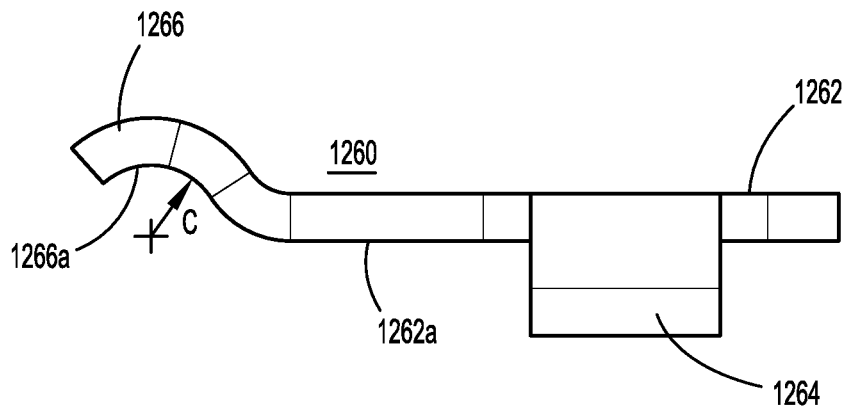
FIG. 20 is a side view of the spring latch of FIG. 19.

With reference to FIGS. 18-20, the backspan 1285b of the spring clip 275b is secured to the release button 275a by spring latch 1260. Specifically, the spring latch 1260 secures the backspan 1285b of the spring clip 275b in a groove 275e defined in an inner surface of the release button 275a.

The spring latch 1260 includes a planar latch body 1262, staking tabs 1264, and retention tabs 1266. The spring latch 1260 may be formed of a metal, e.g., stainless steel 17-4 H900. To form the spring latch 1260, a flat sheet of metal may be cut to the desired shape such that the staking tabs 1264 extend from opposite sides of the latch body 1262 and the retention tabs 1266 extend from an end of the latch body 1262. The staking tabs 1264 are bent downward to be substantially orthogonal to the body 1262. The retention tabs 1266 are bent in an opposite direction of the staking tabs 1264 to a goose neck configuration such that an inner surface 1266a of the retention tabs 1266 are arcuate towards a center of curvature C that is substantially aligned with an inner surface 1262a of the body 1262 as shown in FIG. 20. The center of curvature C may be disposed in a plane defined by the inner surface 1262a of the body 1262.

Figure 21:
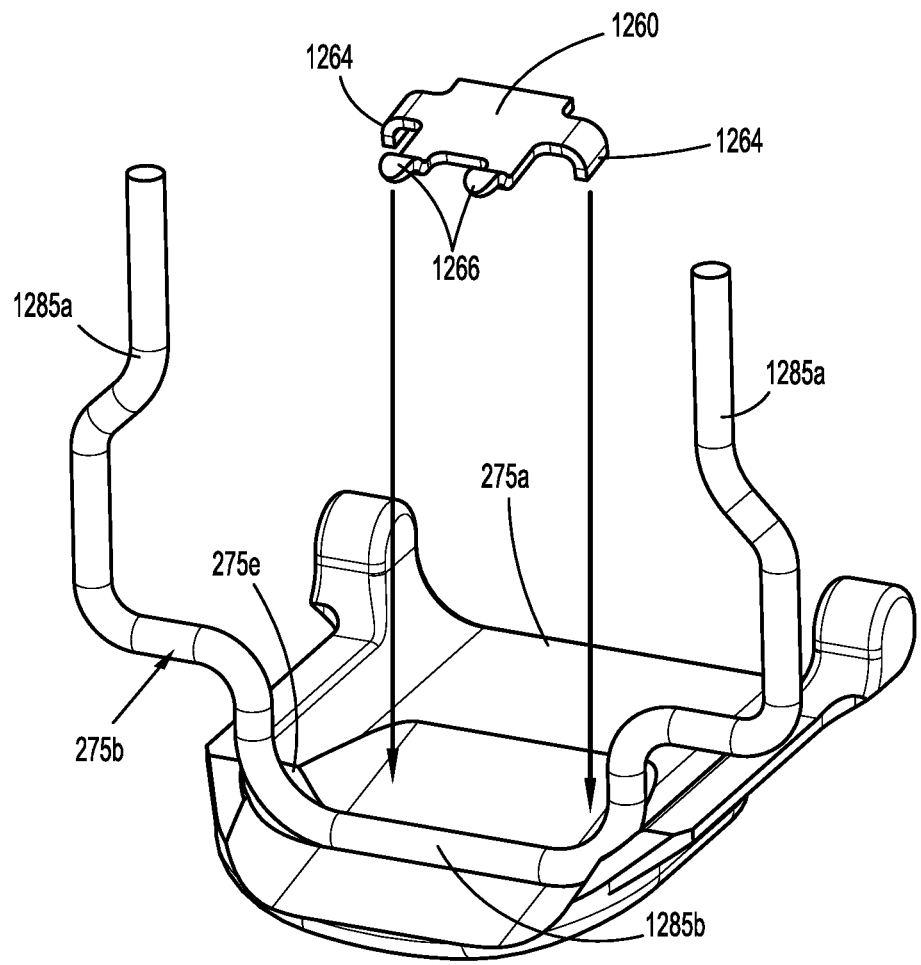
FIG. 21 is a perspective view of the spring latch of FIG. 19 aligned with the inner surface of the release button of FIG. 18 before the spring latch is heat staked into the release button.

Referring to FIG. 21, with the spring latch 1260, staking tabs 1264, and the retention tabs 1266 bent, the spring latch 1260 is aligned with the inner surface of release button 275a with the retention tabs 1266 disposed over the groove 275e of the release button 275a with the backspan 1285b of the spring clip 275b disposed in the groove 275e of the release button 275a. The spring latch 1260 is then heated such that the staking tabs 1264 are above a melting point of the release button 275a. The release button 275a may be formed of a plastic or thermoplastic with a melting point well below a melting point of the spring latch 1260. The staking tabs 1264 of the spring latch 1260 are then driven into the inner surface of the release button 275a such that the staking tabs 1264 are heat staked into the inner surface of the release button 275a to fix the spring latch 1260 to the release button 275a such that the spring clip 275b is secured to the release button 275a and movable in two degrees-of-freedom relative to the release button 275a as shown in FIG. 18. The staking tabs 1264 are driven into the inner surface of the release button 275a until the body 1262 of the spring latch 1260 is in contact with and/or flush with the inner surface of the release button 275a. In some embodiments, the spring latch 1260 is fixed to the release button 275a without the backspan 285b of the spring clip 275b disposed in the groove 275e and with the backspan 285b being positioned in the groove 275e after the spring latch 1260 is fixed to the release button 275a.

In use, when release button 275a is depressed (e.g., in a radially inward direction, FIGS. 15-17), release button 275a moves spring clip 275b transversely relative to trocar assembly 270. As spring clip 275b is moved transversely relative to trocar assembly 270, the pair of legs 1285a of spring clip 275b translate through the pair of lock pins 275c such that a goose-neck in each leg 1285a acts to cam and urge the pair of lock pins 275c radially outward. Specifically, the pair of lock pins 275c are traversed by the gooseneck portions the pair of legs 1285a of spring clip 275b, transitioning from the distal portions thereof to the proximal portions thereof. In so moving, each of the pair of lock pins 275c is urged radially outward by a distance sufficient that each of the pair of lock pins 275c clears respective opening 272a of tubular housing 272, and in an embodiment, project from outer tube 206 or are flush with an outer surface of outer tube 206. It is contemplated that outer tube 206 may include openings 206a (see FIGS. 15 and 17) formed therein which are in registration with each of the pair of lock pins 275c. With the pair of lock pins 275c free and clear of tubular housing 272, trocar assembly 270 may be axially withdrawn from within the distal end of outer tube 206 of adapter assembly 200, or may be inserted into the distal end of outer tube 206 of adapter assembly 200.

Projection of the pair of lock pins 275c, radially outward from outer tube 206 (or to be substantially flush with an outer surface of the outer tube 206), provides a visual indication to the end user that no trocar assembly 270 is inserted into the distal end of outer tube 206 of adapter assembly 200, or that trocar assembly 270 is not properly inserted into the distal end of outer tube 206 of adapter assembly 200. When trocar assembly 270 is properly inserted into the distal end of outer tube 206 of adapter assembly 200, the pair of lock pins 275c of trocar assembly release mechanism 275 are in registration with, and enter into, a respective opening 272a of tubular housing 272 of trocar assembly 270 (see FIG. 23), to thereby lock trocar assembly 270 within the distal end of outer tube 206 of adapter assembly 200, and to thereby provide a visual indication to the end user that trocar assembly 270 is properly inserted into the distal end of outer tube 206 of adapter assembly 200.

Turning now to FIGS. 24-27, in an alternate embodiment, adapter assembly 200 may include a trocar assembly release mechanism or trocar lock assembly 1275. As illustrated, trocar assembly release mechanism 1275 includes a pair of release buttons 1275a rotatably supported on a support block (not shown) and in outer tube 206, via a respective pivot pin 1275e. Each release button 1275a is biased, via a respective biasing member 1275d (e.g., leaf spring), to a locked condition.

Each release button 1275a is identical to one another, and thus, only one of the pair of release buttons 1275a will be described in detail herein. Release button 1275a is substantially semi-circular, extending approximately 180° about pivot pin 1275e. Release button 1275a defines a distal face or surface 1275a' against which a portion of biasing member 1275d engages to urge release button 1275a proximally, and a proximal face or surface projecting to a tail 1275a". An outer surface of release button 1275a may include finger gripping features (e.g., ribs, knurling, etc.) formed thereon.

Release button 1275a is movable between a first unlocked position and a second locked position. If or when a trocar assembly 270 is not properly inserted into the distal end of outer tube 206 of adapter assembly 200, the release button 1275a is rotated or urged radially outward from outer tube 206 by trocar assembly 270, to the first unlocked position, thereby providing a visual indication to the end user that trocar assembly 270 is not properly inserted into the distal end of outer tube 206 of adapter assembly 200. When a trocar assembly 270 is properly inserted into the distal end of outer tube 206 of adapter assembly 200, the release button 1275a is rotated or urged radially inward, to the second locked position, by biasing member 1275d rotating release button 1275a such that tail 1275a" thereof is received in a recess or depression formed in the outer surface of tubular housing 272 of trocar assembly 270 (e.g., similar to openings 272a of tubular housing 272). When release button 1275a is in the second locked position, a visual indication is provided to the end user that trocar assembly 270 is properly inserted and locked into the distal end of outer tube 206 of adapter assembly 200.

Figure 27:
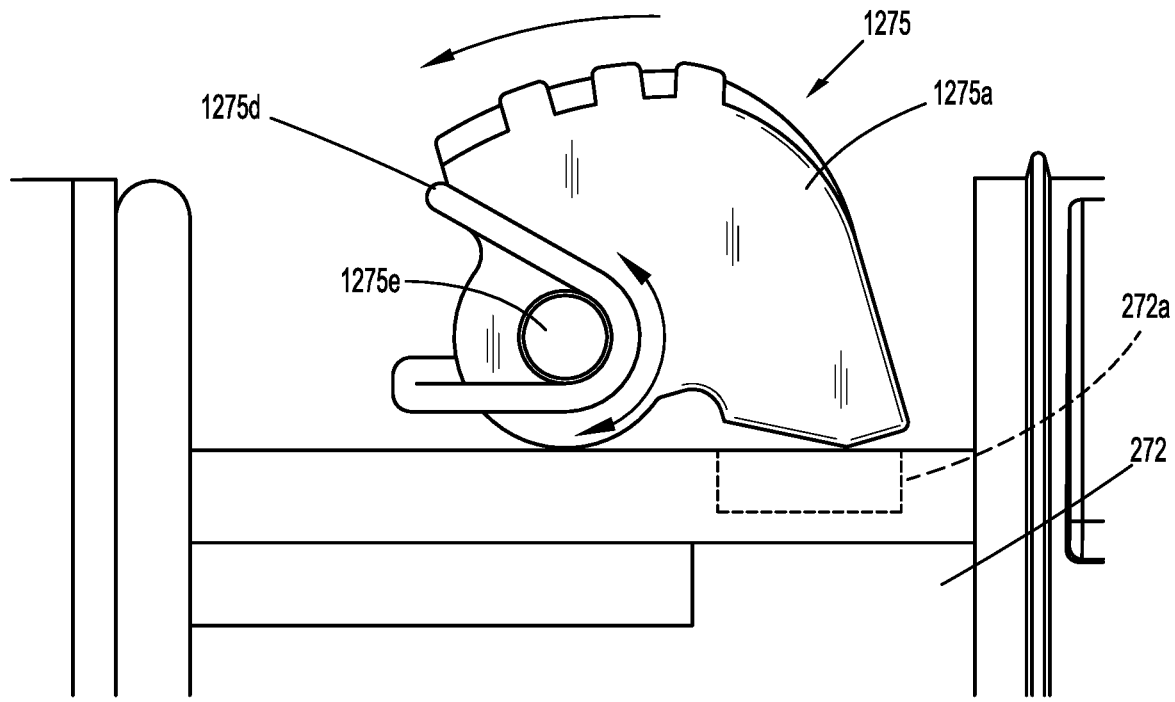
FIG. 27 is an enlarged view of the indicated area of detail of FIG. 26, illustrating the trocar lock assembly in a first unlocked position.
Figure 28:
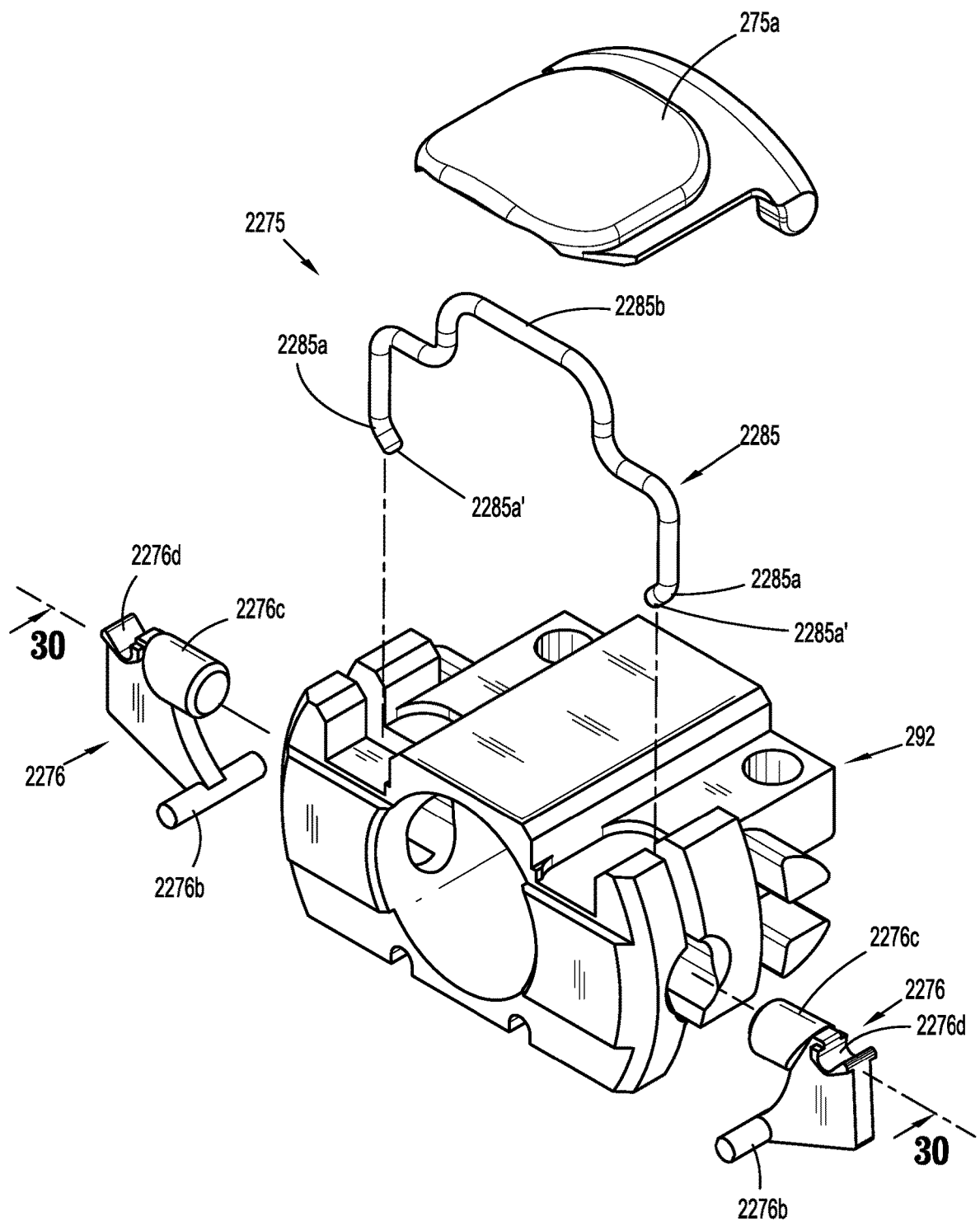
FIG. 28 is a perspective view, with parts separated, of a trocar lock assembly according to another embodiment of the present disclosure.
Figure 29:
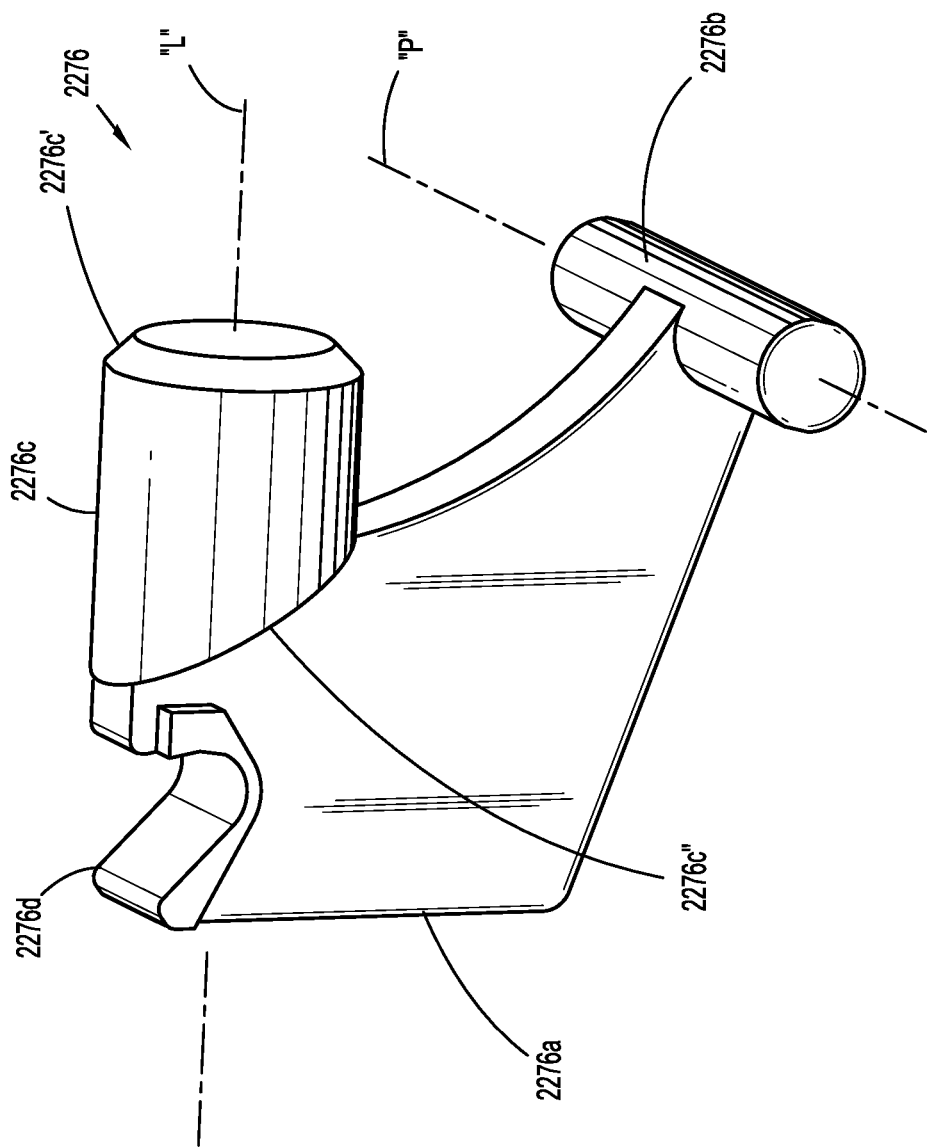
FIG. 29 is an enlarged perspective view of a rocker pin of the trocar lock assembly of FIG. 28.
Figure 30:
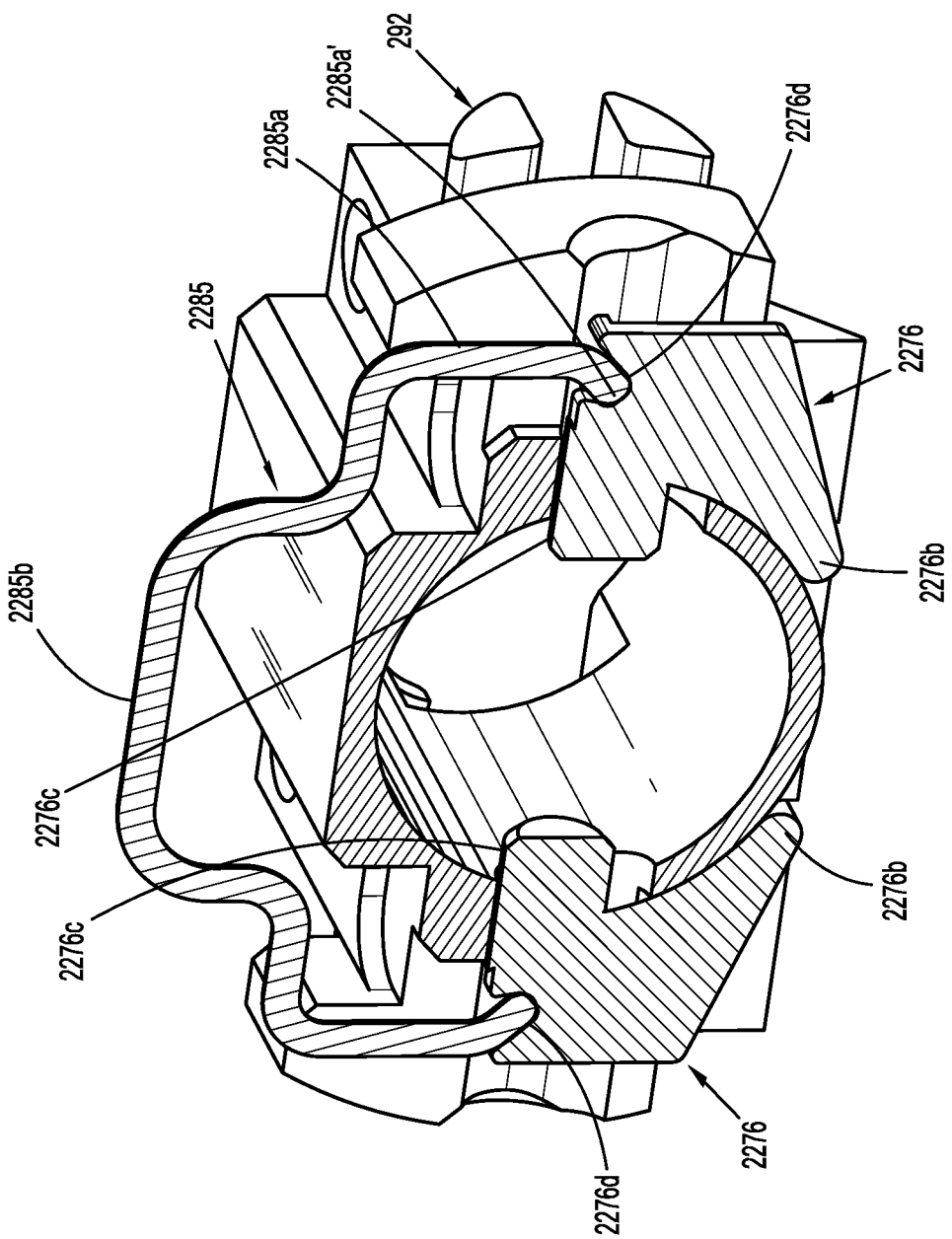
FIG. 30 is a cross-sectional view of the trocar lock assembly of FIG. 28, as taken through 30-30 of FIG. 28, illustrating the trocar lock assembly in a first locked position.
Figure 31:
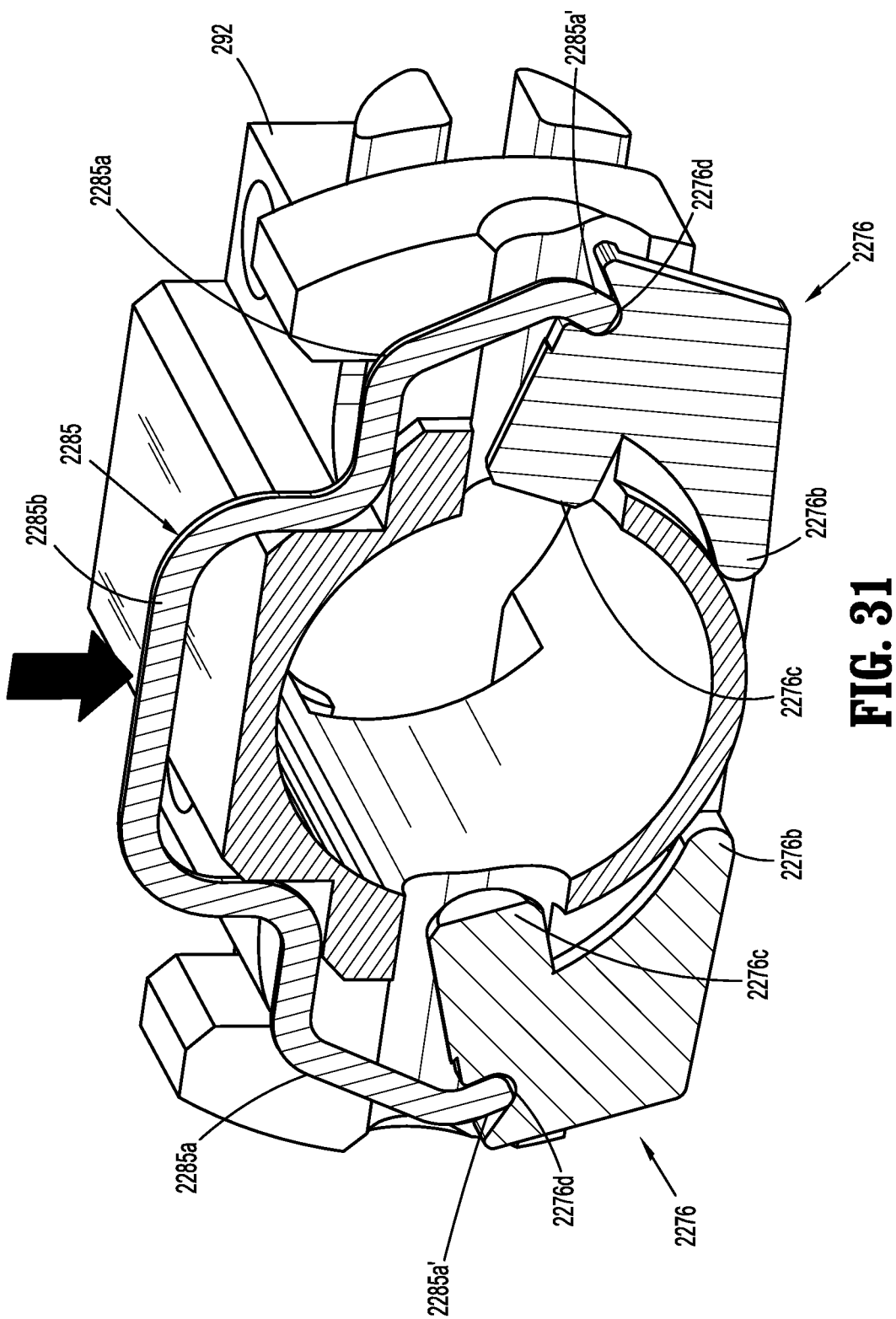
FIG. 31 is a cross-sectional view of the trocar lock assembly of FIG. 28, as taken through 30-30 of FIG. 28, illustrating the trocar lock assembly in a second unlocked position.
Figure 32:
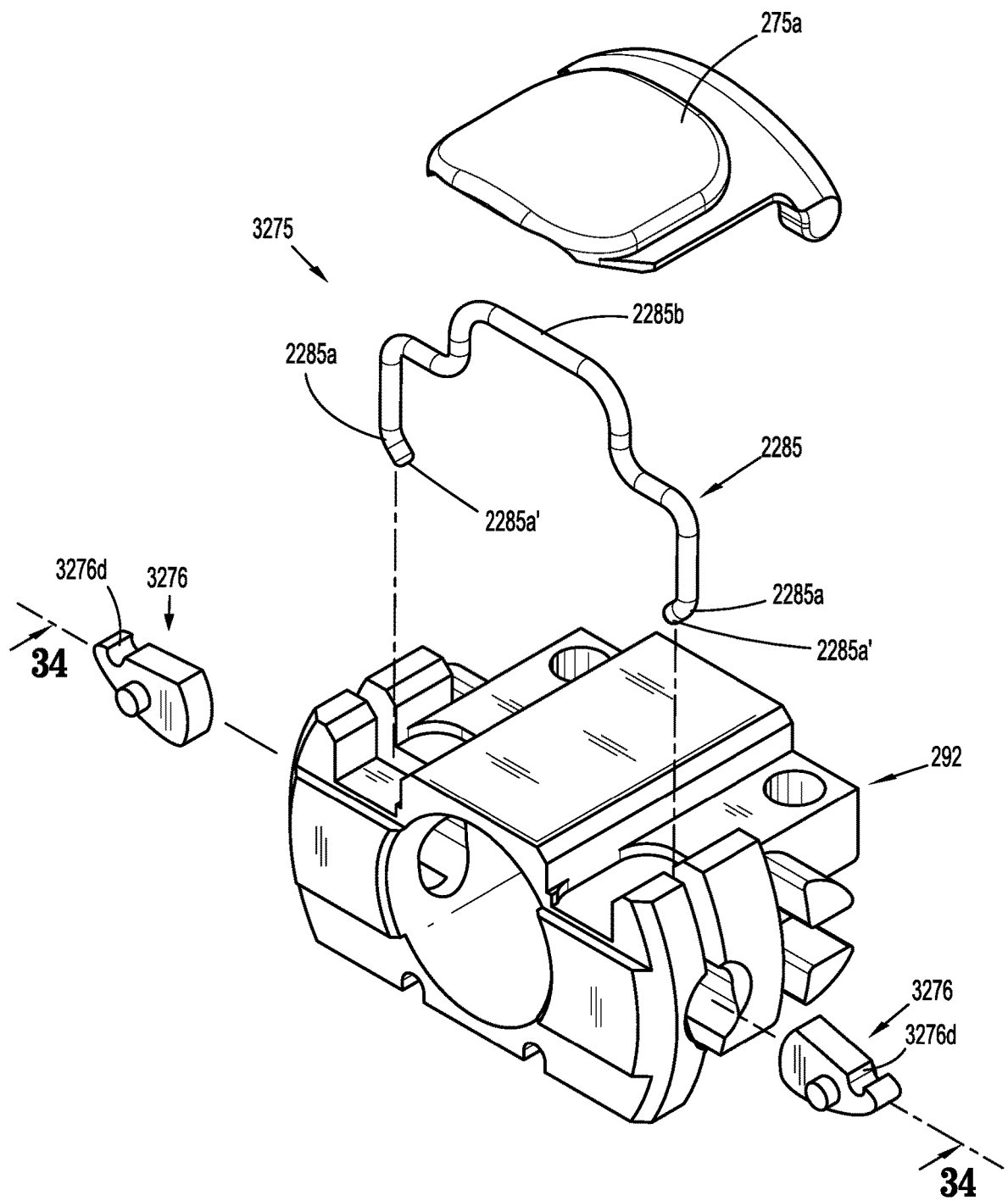
FIG. 32 is a perspective view, with parts separated, of a trocar lock assembly according to yet another embodiment of the present disclosure.
Figure 33:
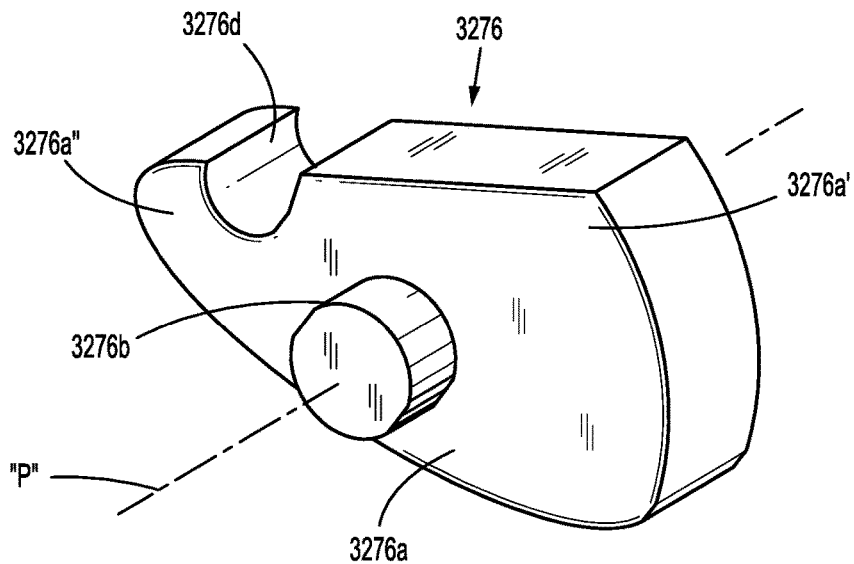
FIG. 33 is an enlarged perspective view of a rocker pin of the trocar lock assembly of FIG. 32.
Figure 34:
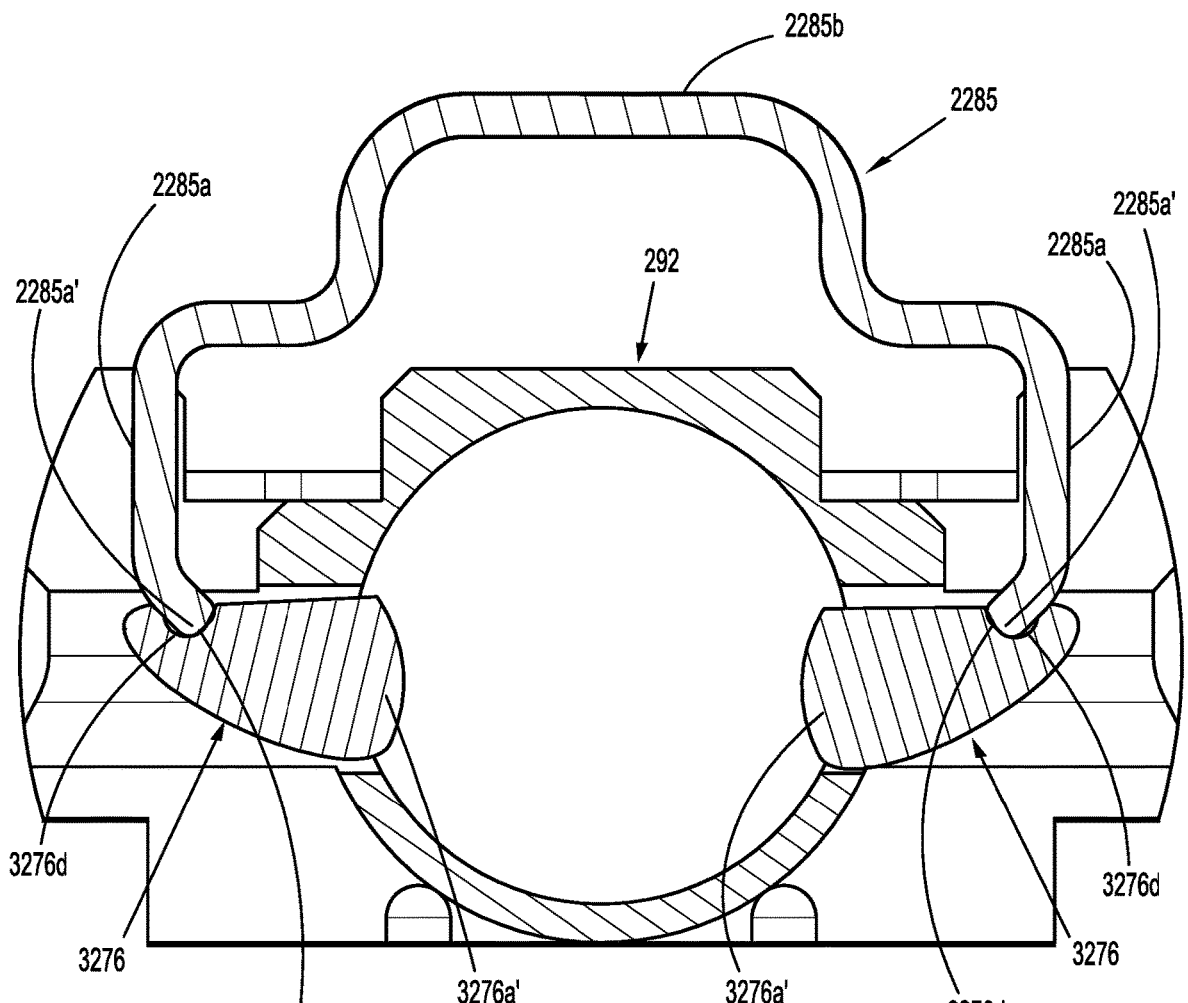
FIG. 34 is a cross-sectional view of the trocar lock assembly of FIG. 32, as taken through 34-34 of FIG. 32, illustrating the trocar lock assembly in a first locked position.
Figure 35:
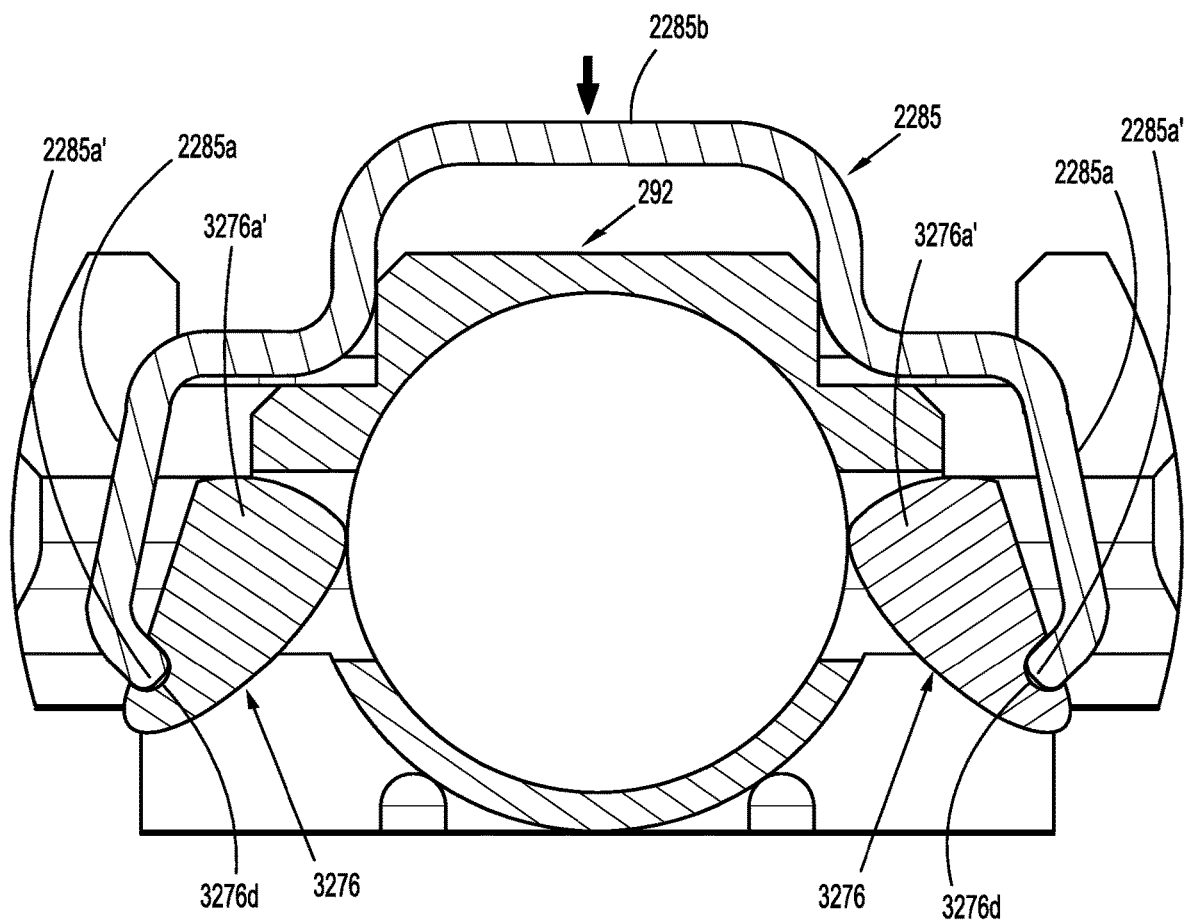
FIG. 35 is a cross-sectional view of the trocar lock assembly of FIG. 32, as taken through 34-34 of FIG. 32, illustrating the trocar lock assembly in a second unlocked position.
Figure 36:
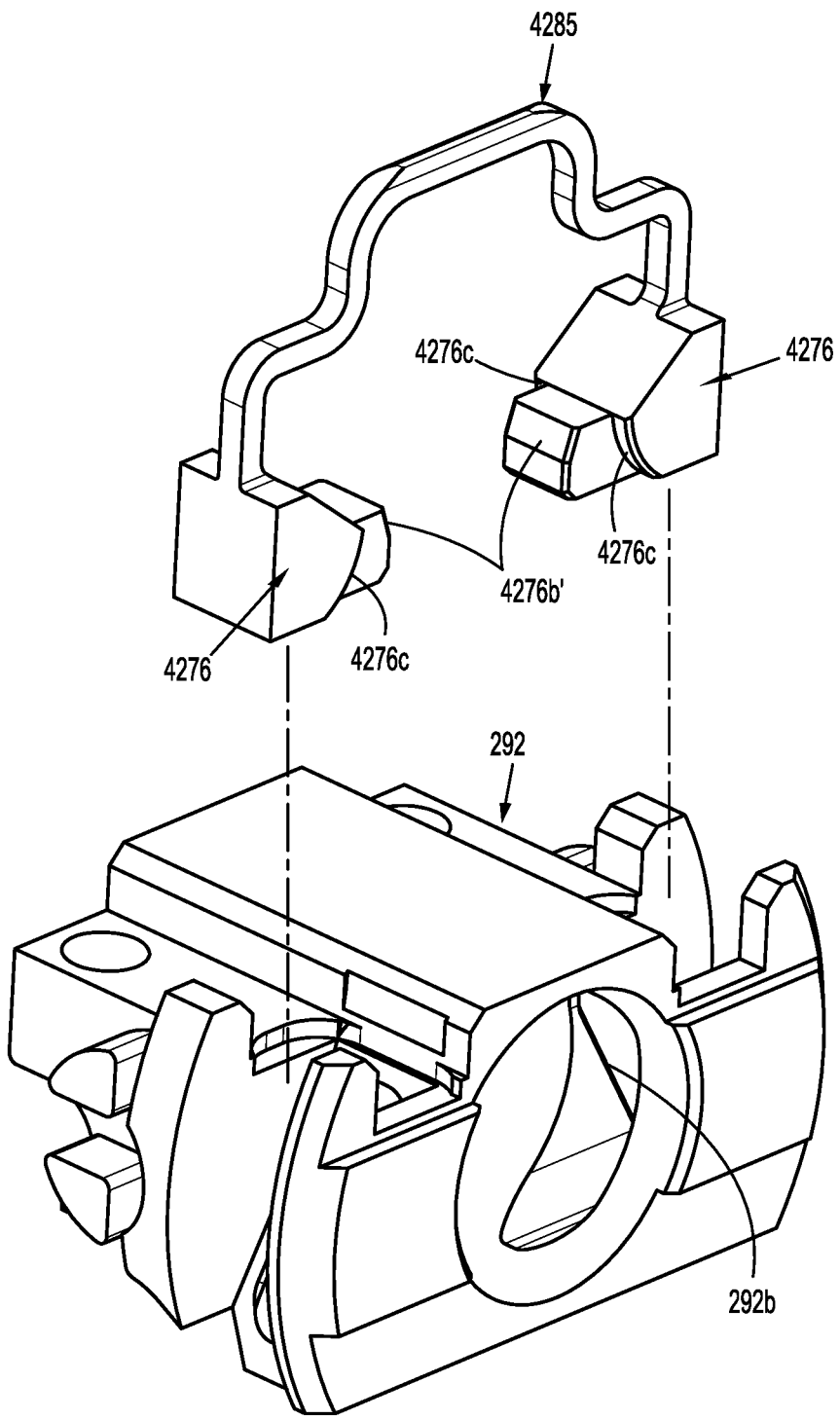
FIG. 36 is a perspective view, with parts separated, of a trocar lock assembly according to still another embodiment of the present disclosure.
Figure 37:
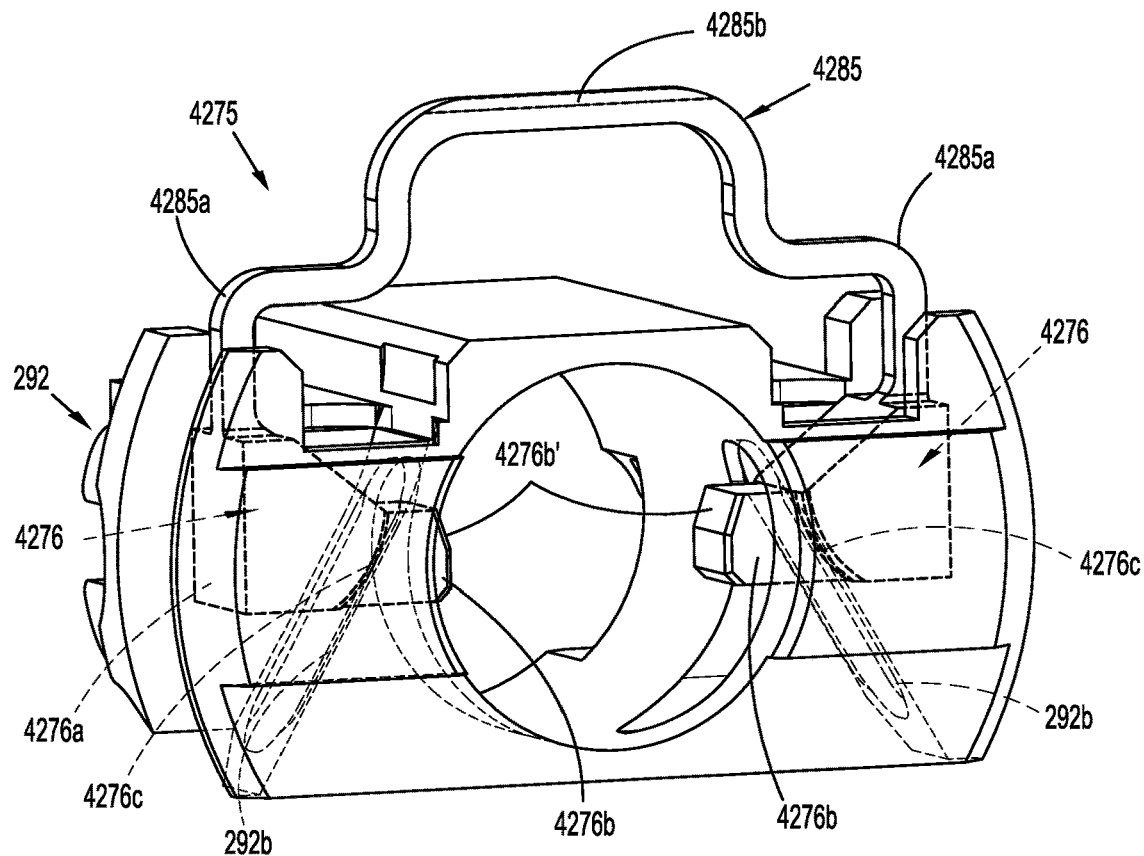
FIG. 37 is a perspective view of the trocar lock assembly of FIG. 36, shown in a first locked position.
Figure 38:
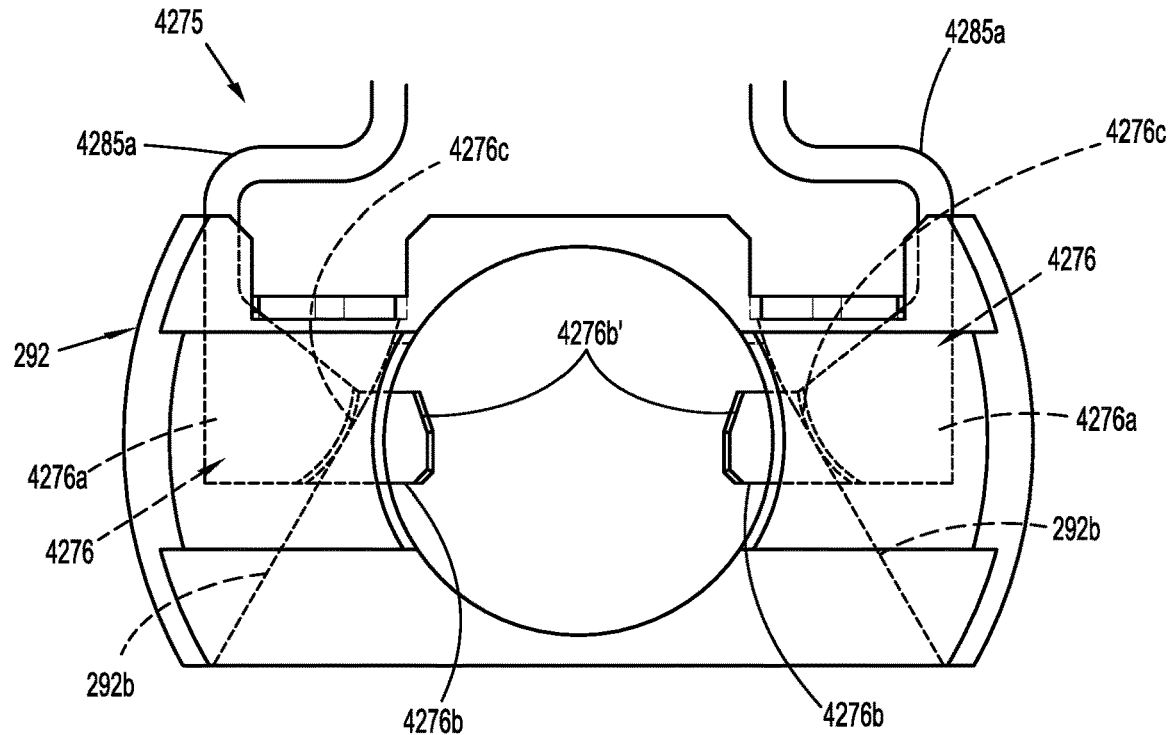
FIG. 38 is a front, elevational view of the trocar lock assembly of FIG. 36, shown in the first locked position of FIG. 37.
Figure 39:
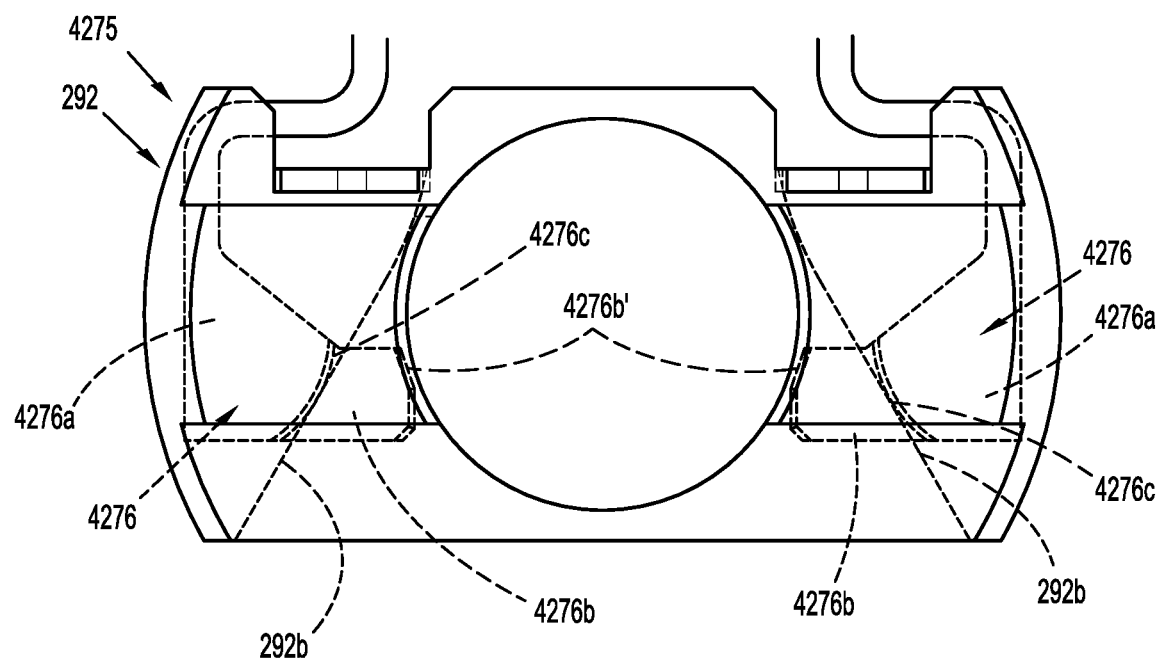
FIG. 39 is a front, elevational view of the trocar lock assembly of FIG. 36, shown in a second unlocked position.

In an embodiment, with reference to FIG. 27, tail 1275a" includes a chamfered distal surface to facilitate receipt or passage of trocar assembly 270 during connection of trocar assembly 270 to outer tube 206, when release button 1275a is in the second locked position. Tail 1275a" further includes a substantially squared proximal surface to inhibit withdrawal or disconnection of trocar assembly 270 from outer tube 206 when release button 1275a is in the second locked position relative to tubular housing 272 of trocar assembly 270.

Turning now to FIGS. 28-31, a trocar assembly release mechanism or trocar lock assembly, according to a further embodiment of the present disclosure, is generally designated as 2275. Trocar assembly release mechanism 2275 includes a release button 275a pivotally supported on a hinge guide 293 (see FIGS. 12-17) and in outer tube 206. Release button 275a is biased, via a spring 275d (see FIGS. 14, 22, and 23), to a locked/extended condition.

Figure 8:
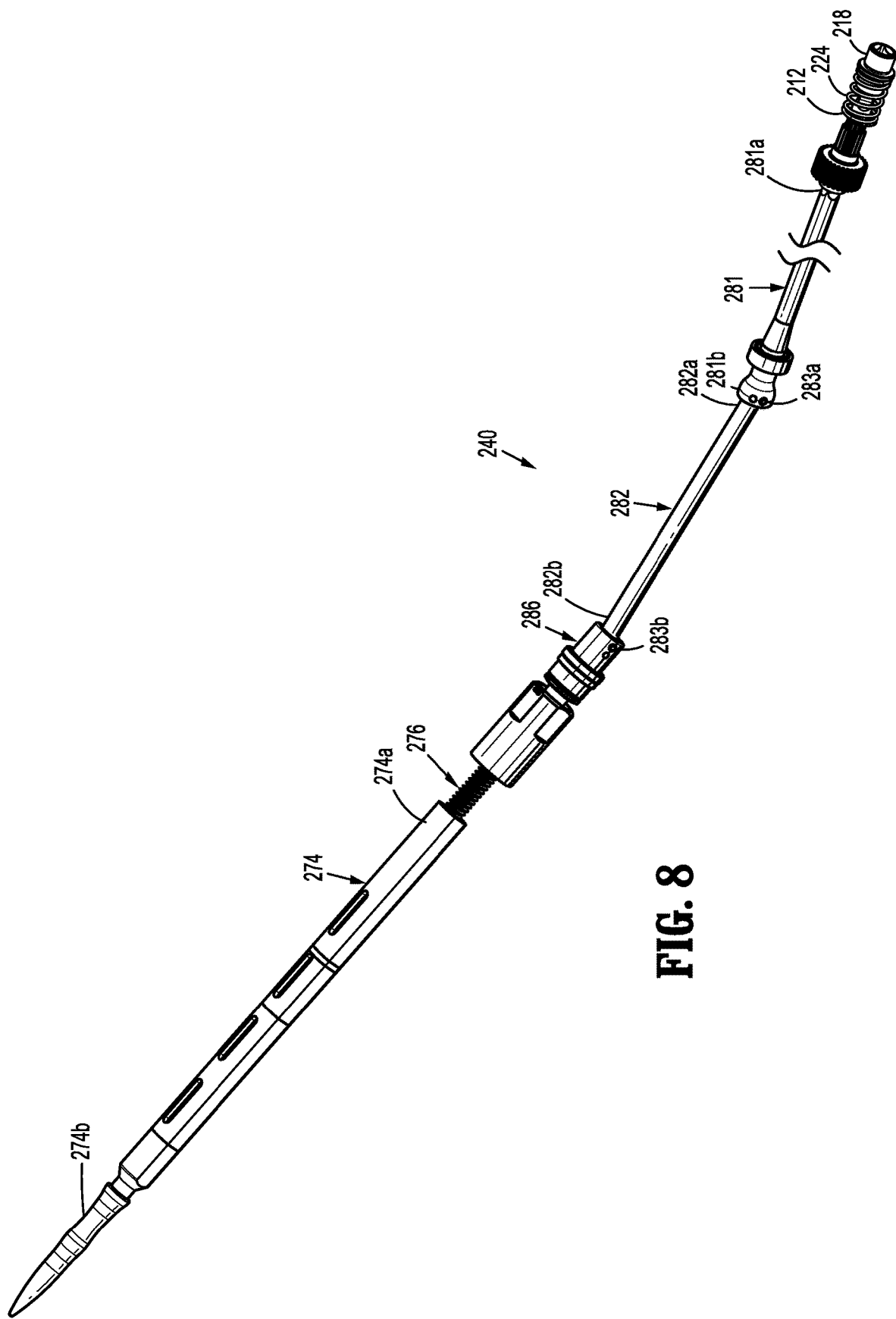
FIG. 8 is a perspective view of the first force/rotation transmitting/converting assembly of FIG. 7.
Figure 9:
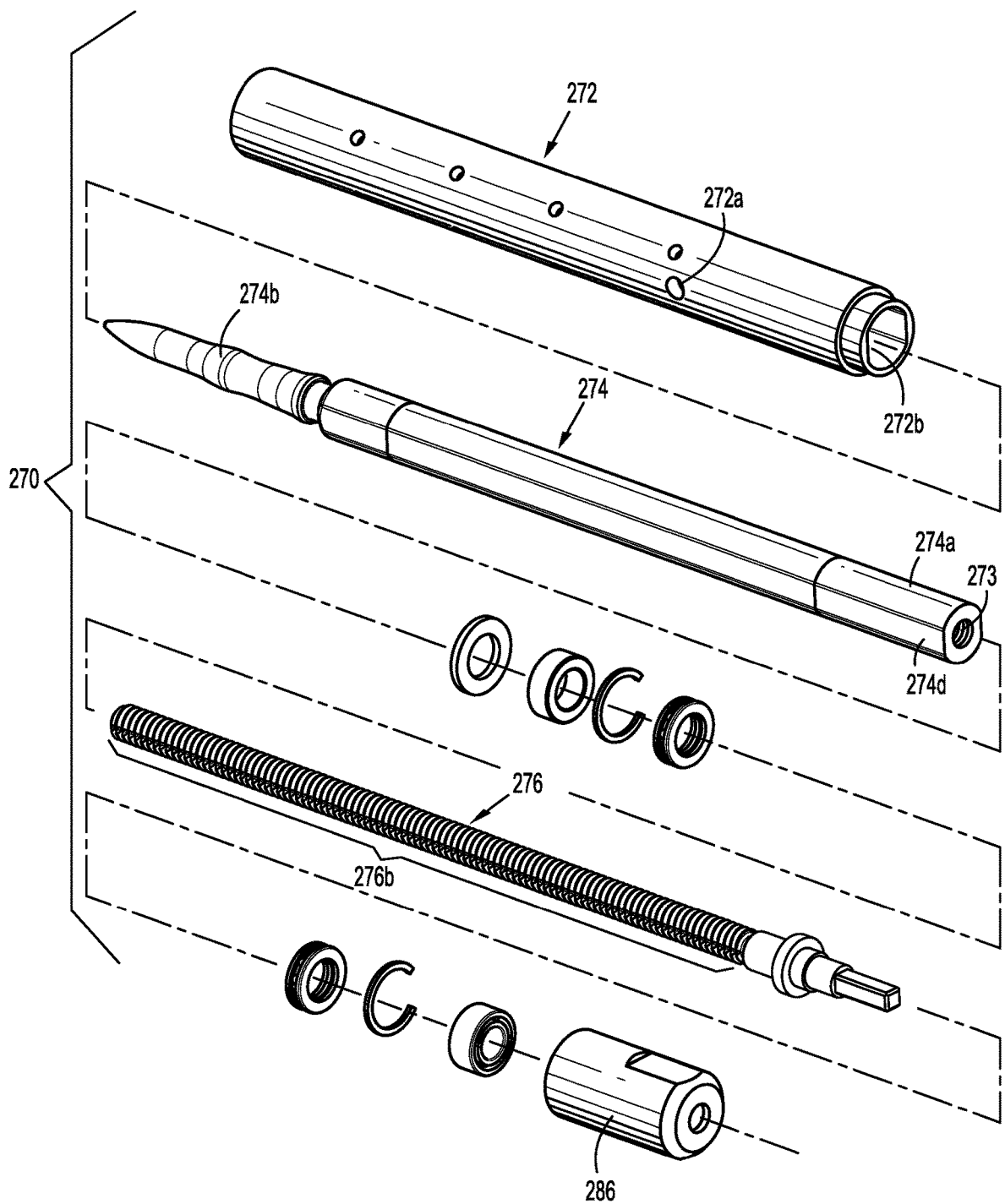
FIG. 9 is a perspective view, with parts separated, of a trocar assembly of the first force/rotation transmitting/converting assembly of FIG. 7.
Figure 12:
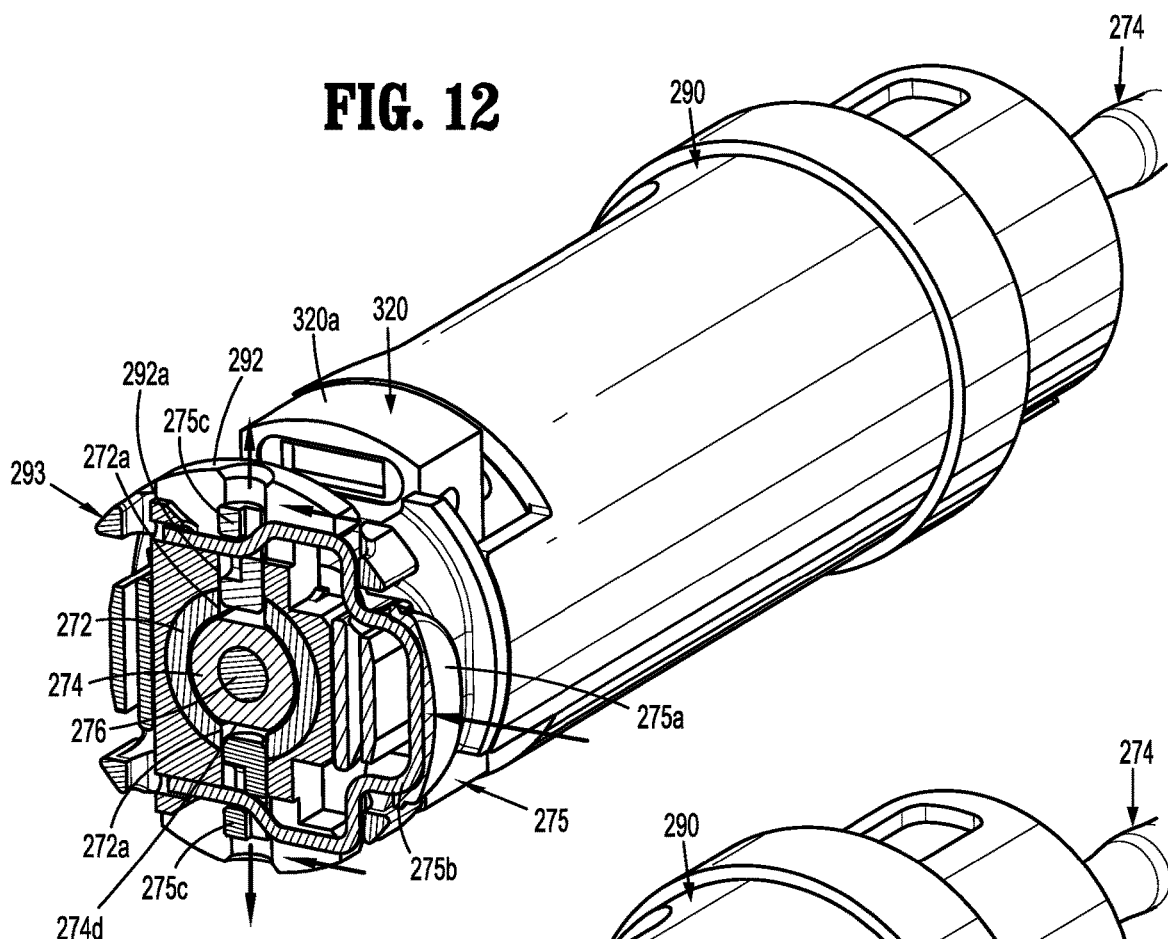
FIG. 12 is a cross-sectional view as taken through 12-12 of FIG. 10.
Figure 13:
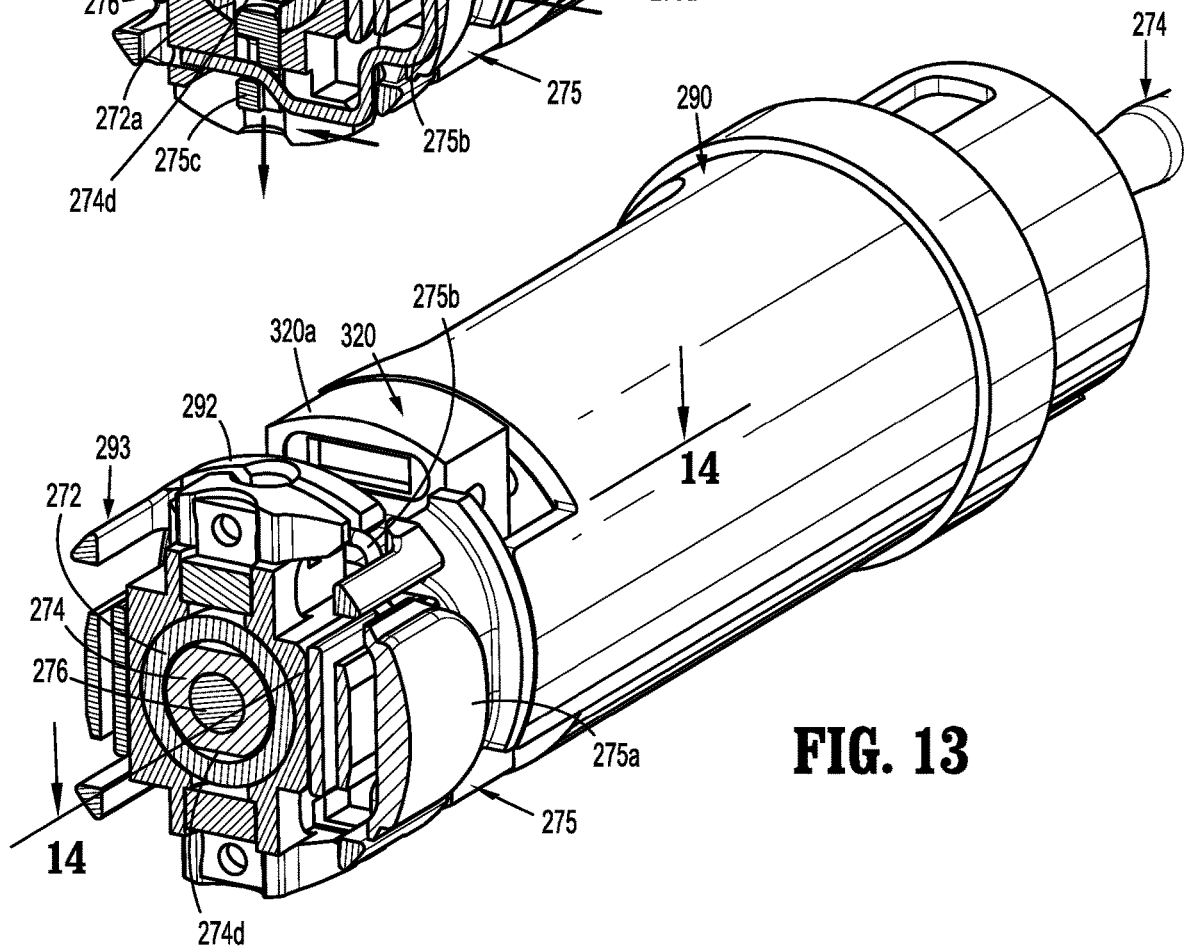
FIG. 13 is a cross-sectional view as taken through 13-13 of FIG. 10.
Figure 14:
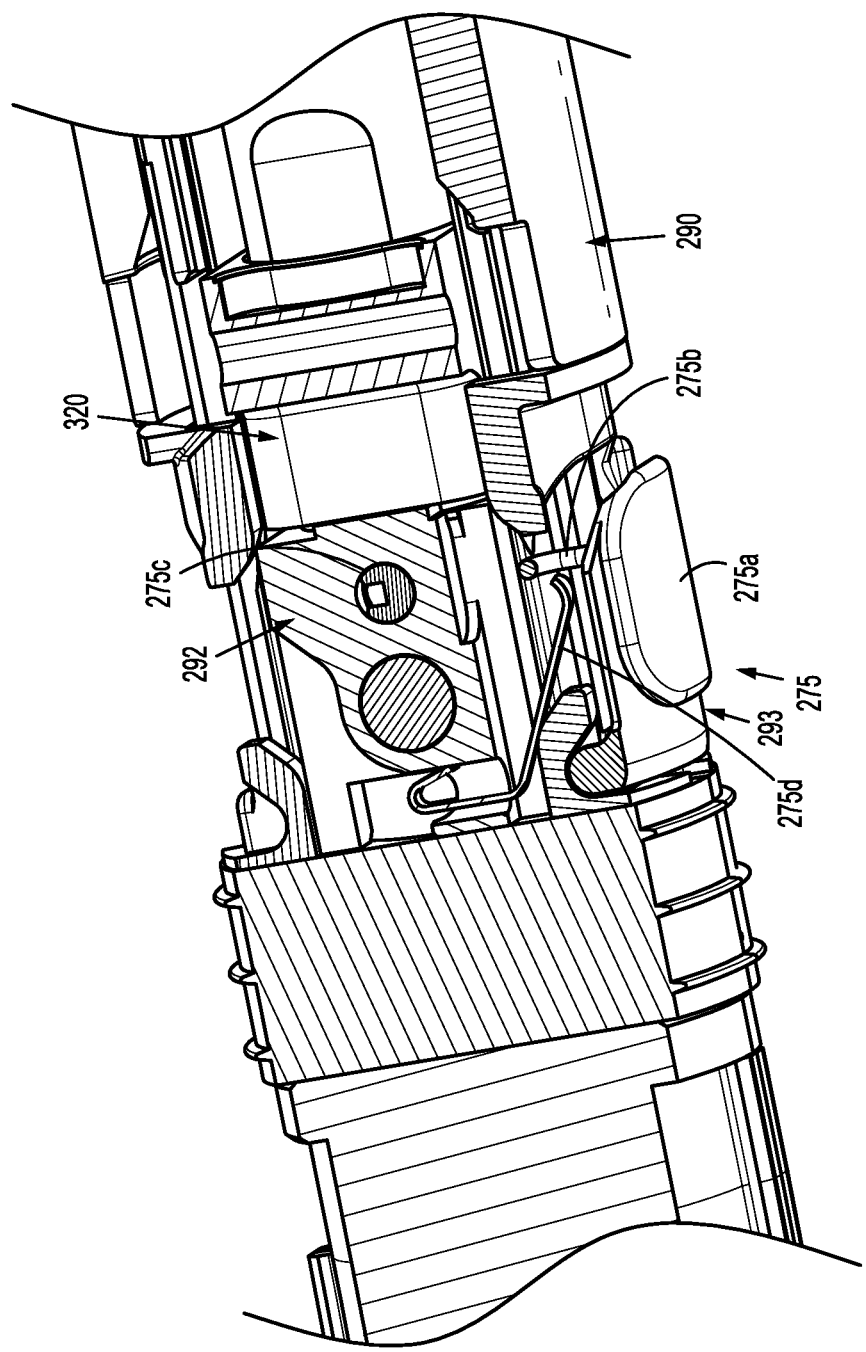
FIG. 14 is a cross-sectional view as taken through 14-14 of FIG. 13.
Figure 15:
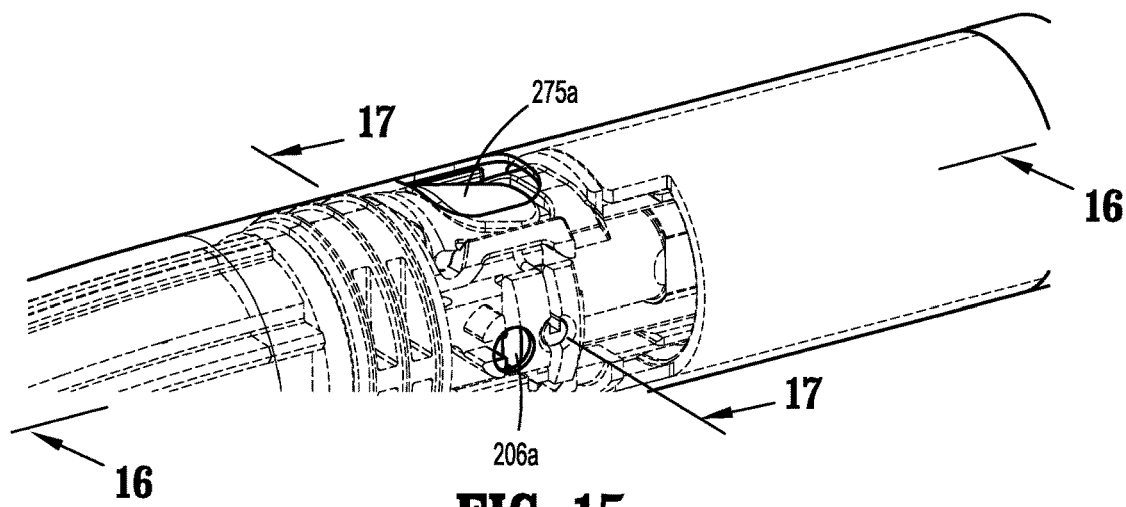
FIG. 15 is an enlarged view of the indicated area of detail of FIG. 4.
Figure 16:
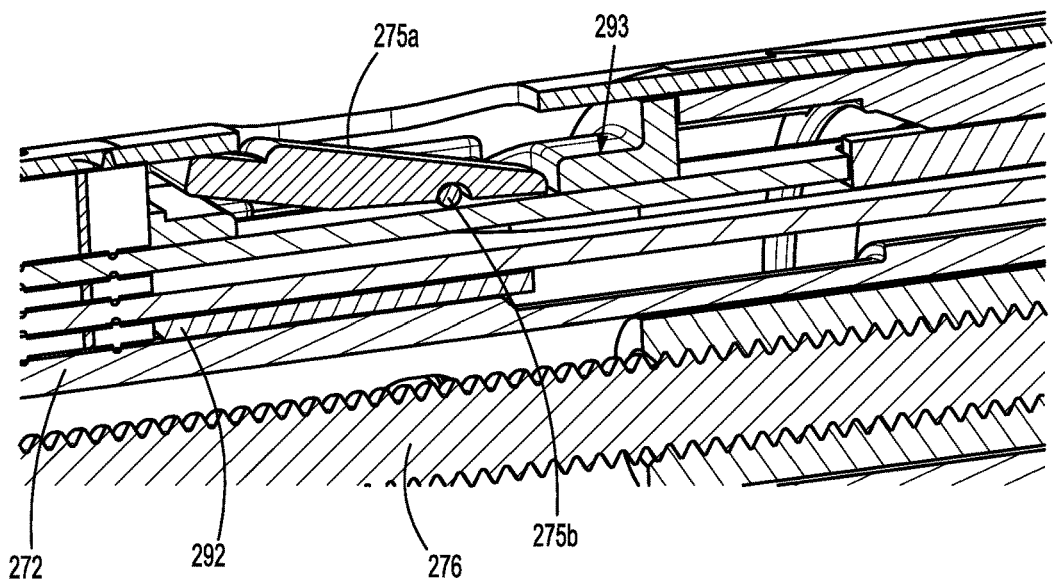
FIG. 16 is a cross-sectional view as taken through 16-16 of FIG. 15.
Figure 17:
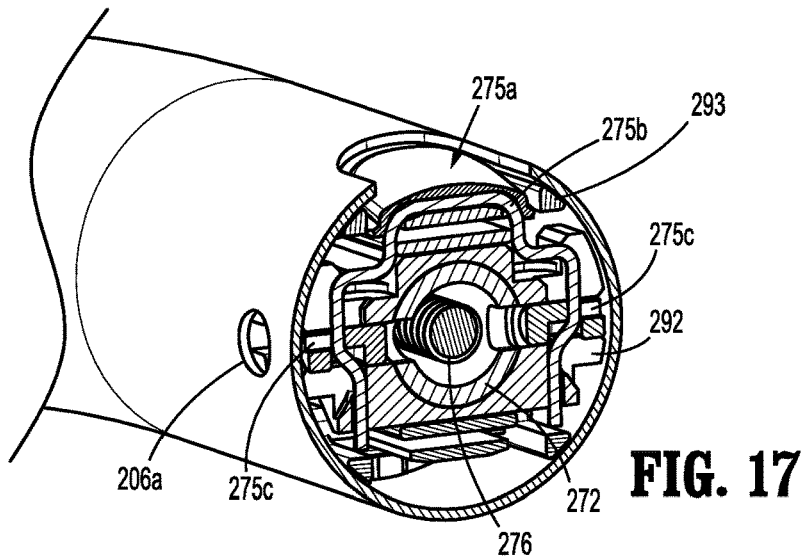
FIG. 17 is a cross-sectional view as taken through 17-17 of FIG. 15.

Trocar assembly release mechanism 2275 further includes a spring clip 2285 having a backspan 2285b connected to release button 275a, and a pair of legs 2285a, extending from the backspan 2285b, that extend through support block 292 and transversely across trocar assembly 270 (see FIGS. 8 and 9). Each of the pair of legs 2285a of spring clip 2285 extends into contact with a respective lock rocker pin 2276. Specifically, each of the pair of legs 2285a of spring clip 2285 includes a free end 2285a', having a curved profile, for engagement in a respective pocket 2276d defined in rocker pin 2276 (as described in greater detail below).

Trocar assembly release mechanism 2275 includes a pair of rocker pins 2276 pivotably supported within support block 292, and configured and dimensioned to selectively engage respective radially oriented openings 272a of tubular housing 272 of trocar assembly 270 (see FIGS. 8 and 9) to axially and rotationally fix tubular housing 272 within outer tube 206 of adapter assembly 200. Each rocker pin 2276 is identical to one another, and thus, only one of the pair of rocker pins 2276 will be described in detail herein.

With continued reference to FIGS. 28-31, rocker pin 2276 includes a body portion 2276a which defines a body plane, a boss 2276b connected to body portion 2276a which defines a pivot axis "P" extending orthogonal to the body plane, and a lock shaft 2276c connected to body portion 2276a which defines a lock axis "L" extending in and co-parallel with the body plane, and orthogonal to and radially spaced from the pivot axis "P". Lock shaft 2276c has a substantially circular transverse cross-sectional profile including a chamfered distal annular face 2276c' and a chiseled proximal face 2276c". Chamfered distal annular face 2276c' facilitates introduction of lock shaft 2276c into respective radially oriented opening 272a of tubular housing 272 of trocar assembly 270. It is contemplated that a plane defined by chiseled proximal face 2276c" of lock shaft 2276c extends substantially towards or through pivot axis "P" of boss 2276b.

Rocker pin 2276 may include a pocket 2276d formed in body portion 2276a and being disposed proximal of lock shaft 2276c, and a location substantially opposite of boss 2276b. Pocket 2276d is configured and dimensioned to engage or receive free end 2285a' of spring clip 2285.

In use, when release button 275a is depressed (e.g., in a radially inward direction, FIGS. 15-17 and 31), to the first unlocked position, release button 275a moves spring clip 2285 transversely relative to trocar assembly 270. As spring clip 2285 is moved transversely relative to trocar assembly 270, the free ends 2285a' of the pair of legs 2285a of spring clip 2285 press on rocker pins 2276, via respective pockets 2276d, to urge the pair of rocker pins 2276, via a pivoting motion about bosses 2276b, radially outward. Specifically, lock shafts 2276c of rocker pins 2276 are caused to be withdrawn from within respective openings 272a of tubular housing 272 of trocar assembly 270. In so moving, as rocker pins 2276 rotate, and since the free ends 2285a' of the pair of legs 2285a of spring clip 2285 are disposed within respective pockets 2276d, the pair of legs 2285a of spring clip 2285 are caused to be splayed outwardly, creating a spring bias therein. With the lock shafts 2276c of rocker pins 2276 free and clear of tubular housing 272, trocar assembly 270 may be axially withdrawn from within the distal end of outer tube 206 of adapter assembly 200, or may be inserted into the distal end of outer tube 206 of adapter assembly 200.

When trocar assembly 270 is properly inserted into the distal end of outer tube 206 of adapter assembly 200, the lock shafts 2276c of rocker pins 2276 of trocar assembly release mechanism 2275 are in registration with, and free to enter into, a respective opening 272a of tubular housing 272 of trocar assembly 270.

Due to the spring bias created in the pair of legs 2285a of spring clip 2285, when release button 275a is pressed, upon a release of release button 275a, to the second locked position, the pair of legs 2285a of spring clip 2285 urge the lock shafts 2276c of rocker pins 2276 radially inward towards one another, to enter respective openings 272a of tubular housing 272 of trocar assembly 270 (see FIG. 9), to thereby lock trocar assembly 270 within the distal end of outer tube 206 of adapter assembly 200.

Turning now to FIGS. 32-35, a trocar assembly release mechanism or trocar lock assembly, according to a further embodiment of the present disclosure, is generally designated as 3275. Trocar assembly release mechanism 3275 is substantially similar to trocar assembly release mechanism 2275, and thus, in the interest of efficiency, only the differences therebetween will be described in detail herein.

Trocar assembly release mechanism 3275 includes a spring clip 2285 having a pair of legs 2285a, extending from a backspan 2285b, that extend through support block 292 and transversely across trocar assembly 270 (see FIGS. 8 and 9). Each of the pair of legs 2285a of spring clip 2285 extends into contact with a respective lock rocker cam 3276. Specifically, each of the pair of legs 2285a of spring clip 2285 includes a free end 2285a', having a curved profile, for engagement in a respective pocket 3276d defined in rocker cam 3276 (as described in greater detail below).

Trocar assembly release mechanism 3275 includes a pair of rocker cams 3276 pivotably supported within support block 292, and configured and dimensioned to selectively engage respective radially oriented openings 272a of tubular housing 272 of trocar assembly 270 (see FIGS. 8 and 9) to axially and rotationally fix tubular housing 272 within outer tube 206 of adapter assembly 200. Each rocker cam 3276 is identical to one another, and thus, only one of the pair of rocker cams 3276 will be described in detail herein.

With continued reference to FIGS. 32-35, rocker cam 3276 includes a body portion 3276a which defines a body plane. Body portion 3276a has a substantially tear-drop profile including an enlarged head portion 3276a' and a narrowed tail portion 3276a". Rocker cam 3276 further includes a boss 3276b projecting from body portion 3276a which defines a pivot axis "P" extending orthogonal to the body plane. Boss 3276b is located substantially mid-way between enlarged head portion 3276a' and narrowed tail portion 3276a" of body portion 3276a. Rocker cam 3276 includes a pocket 3276d formed in narrowed tail portion 3276a" of body portion 3276a and being disposed proximal of boss 3276b. Pocket 3276d is configured and dimensioned to engage or receive free end 2285a' of spring clip 2285.

In use, when release button 275a is depressed (e.g., in a radially inward direction, FIGS. 15-17 and 31), to the first unlocked position, release button 275a moves spring clip 2285 transversely relative to trocar assembly 270. As spring clip 2285 is moved transversely relative to trocar assembly 270, the free ends 2285a' of the pair of legs 2285a of spring clip 2285 press on rocker cams 3276, via respective pockets 3276d, to urge the pair of rocker cams 3276, via a pivoting motion about bosses 3276b, radially outward. Specifically, enlarged head portion 3276a' of rocker cams 3276 are caused to be withdrawn from within or rotated out of respective openings 272a of tubular housing 272 of trocar assembly 270. In so moving, as rocker cams 3276 rotate, and since the free ends 2285a' of the pair of legs 2285a of spring clip 2285 are disposed within respective pockets 3276d, the pair of legs 2285a of spring clip 2285 are caused to be splayed outwardly, creating a spring bias therein. With the enlarged head portion 3276a' of rocker cams 3276 free and clear of tubular housing 272, trocar assembly 270 may be axially withdrawn from within the distal end of outer tube 206 of adapter assembly 200, or may be inserted into the distal end of outer tube 206 of adapter assembly 200.

When trocar assembly 270 is properly inserted into the distal end of outer tube 206 of adapter assembly 200, the enlarged head portion 3276a' of rocker cams 3276 of trocar assembly release mechanism 3275 are in registration with, and free to enter into, a respective opening 272a of tubular housing 272 of trocar assembly 270.

Due to the spring bias created in the pair of legs 2285a of spring clip 2285, when release button 275a is pressed, upon a release of release button 275a, to the second locked position, the pair of legs 2285a of spring clip 2285 urge the enlarged head portion 3276a' of rocker cams 3276 radially inward towards one another, to enter respective openings 272a of tubular housing 272 of trocar assembly 270 (see FIG. 9), to thereby lock trocar assembly 270 within the distal end of outer tube 206 of adapter assembly 200.

Turning now to FIGS. 36-39, a trocar assembly release mechanism or trocar lock assembly, according to a further embodiment of the present disclosure, is generally designated as 4275. Trocar assembly release mechanism 4275 includes a release button 275a pivotally supported on a hinge guide 293 (see FIGS. 12-17) and in outer tube 206. Release button 275a is biased, via a spring 275d (see FIGS. 14, 22, and 23), to a locked/extended condition.

Trocar assembly release mechanism 4275 further includes a spring clip 4285 having a backspan 4285b connected to release button 275a, and a pair of legs 4285a, extending from the backspan 4285b, that extend through support block 292 and transversely across trocar assembly 270 (see FIGS. 8 and 9). Each of the pair of legs 4285a of spring clip 4285 supports a respective sliding lock cam pin 4276.

Each lock cam pin 4276 of trocar assembly release mechanism 4275 is slidably supported within support block 292, and configured and dimensioned to selectively engage respective radially oriented openings 272a of tubular housing 272 of trocar assembly 270 (see FIGS. 8 and 9) to axially and rotationally fix tubular housing 272 within outer tube 206 of adapter assembly 200. Each lock cam pin 4276 is identical to one another, and thus, only one of the pair of lock cam pins 4276 will be described in detail herein.

With continued reference to FIGS. 36-39, lock cam pin 4276 includes a body portion 4276a which defines a body plane, a lock boss, shaft or nose 4276b connected to body portion 4276a extending from body portion 4276a, and a cam surface 4276c formed in or projecting from the body plane of body portion 4276a, at a location between substantially between body portion 4276a and lock boss 4276b.

Lock boss 4276b has a substantially rectangular transverse cross-sectional profile including a chamfered distal face 4276b'. Chamfered distal face 4276b' facilitates introduction of lock boss 4276b into respective radially oriented opening 272a of tubular housing 272 of trocar assembly 270.

As illustrated in FIGS. 36-39, support block 292 includes camming surfaces 292b formed therein and associated with respective lock cam pins 4276. Each camming surface 292b is configured to engage and act on cam surfaces 4276c of respective lock cam pins 4276.

In use, when release button 275a is depressed (e.g., in a radially inward direction, FIGS. 15-17 and 31), to the first unlocked position, release button 275a moves spring clip 4285 transversely relative to trocar assembly 270. As spring clip 4285 is moved transversely relative to trocar assembly 270, lock cam pins 4276 of trocar assembly release mechanism 4275, supported on the pair of legs 4285a of spring clip 4285, are caused to be translated relative to support block 292. As lock cam pins 4276 translate relative to support block 292, cam surfaces 4276c of lock cam pins 4276 engage respective camming surfaces 292b of support block 292, which in turn causes lock cam pins 4276 to translated radially outward or relatively away from one another.

As lock cam pins 4276 translate radially outward from one another, lock bosses 4276b of lock cam pins 4276 are caused to be withdrawn from within respective openings 272a of tubular housing 272 of trocar assembly 270. With lock cam pins 4276 of trocar assembly release mechanism 4275 free and clear of tubular housing 272, trocar assembly 270 may be axially withdrawn from within the distal end of outer tube 206 of adapter assembly 200, or may be inserted into the distal end of outer tube 206 of adapter assembly 200. Also, as lock cam pins 4276 translate radially outward from one another, the pair of legs 4285a of spring clip 4285 are caused to be splayed apart from one another, creating a spring bias therein.

When trocar assembly 270 is properly inserted into the distal end of outer tube 206 of adapter assembly 200, lock cam pins 4276 of trocar assembly release mechanism 4275 are in registration with, and/or free to enter into, a respective opening 272a of tubular housing 272 of trocar assembly 270.

Due to the spring bias created in the pair of legs 4285a of spring clip 4285, when release button 275a is pressed, upon a release of release button 275a, to the second locked position, the pair of legs 4285a of spring clip 4285 urge the lock cam pins 4276 of trocar assembly release mechanism 4275 radially inward towards one another, to enter respective openings 272a of tubular housing 272 of trocar assembly 270 (see FIG. 9), to thereby lock trocar assembly 270 within the distal end of outer tube 206 of adapter assembly 200.

With reference to FIGS. 1-9, in operation, the first force/rotation transmitting/converting assembly 240 functions to advance/retract trocar member 274 of trocar assembly 270 of the adapter assembly 200, and to open/close the reload 400 (FIG. 1) when an anvil assembly 510 is connected to the trocar member 274. Specifically, as the first rotatable proximal drive shaft 212 is rotated, due to a rotation of the first connector sleeve 218, as a result of the rotation of the first coupling shaft 124a (FIG. 2) of the handle assembly 100, the second rotatable proximal drive shaft 281 is caused to be rotated. Rotation of the second rotatable proximal drive shaft 281 results in contemporaneous rotation of the rotatable distal drive shaft 282. Rotation of the rotatable distal drive shaft 282 causes contemporaneous rotation of the coupling member 286, which, in turn, causes contemporaneous rotation of the drive screw 276 of the trocar assembly 270. As the drive screw 276 is rotated within and relative to the trocar member 274, engagement between the trocar member 274 and the drive screw 276 (e.g., threaded engagement) causes axial translation of the trocar member 274 within the tubular housing 272 of the trocar assembly 270. Specifically, rotation of the drive screw 276 in a first direction causes axial translation of the trocar member 274 in a first direction (e.g., extension or advancement of the trocar assembly 270), and rotation of the drive screw 276 in a second direction causes axial translation of the trocar member 274 in a second direction (e.g., retraction of the trocar assembly 270). When the anvil assembly 510 is connected to the trocar member 274, the axial translation of the trocar member 274 in the first direction results in an opening of the reload 400, and the axial translation of the trocar member 274 in the second direction results in a closing of the reload 400.

Figure 40:
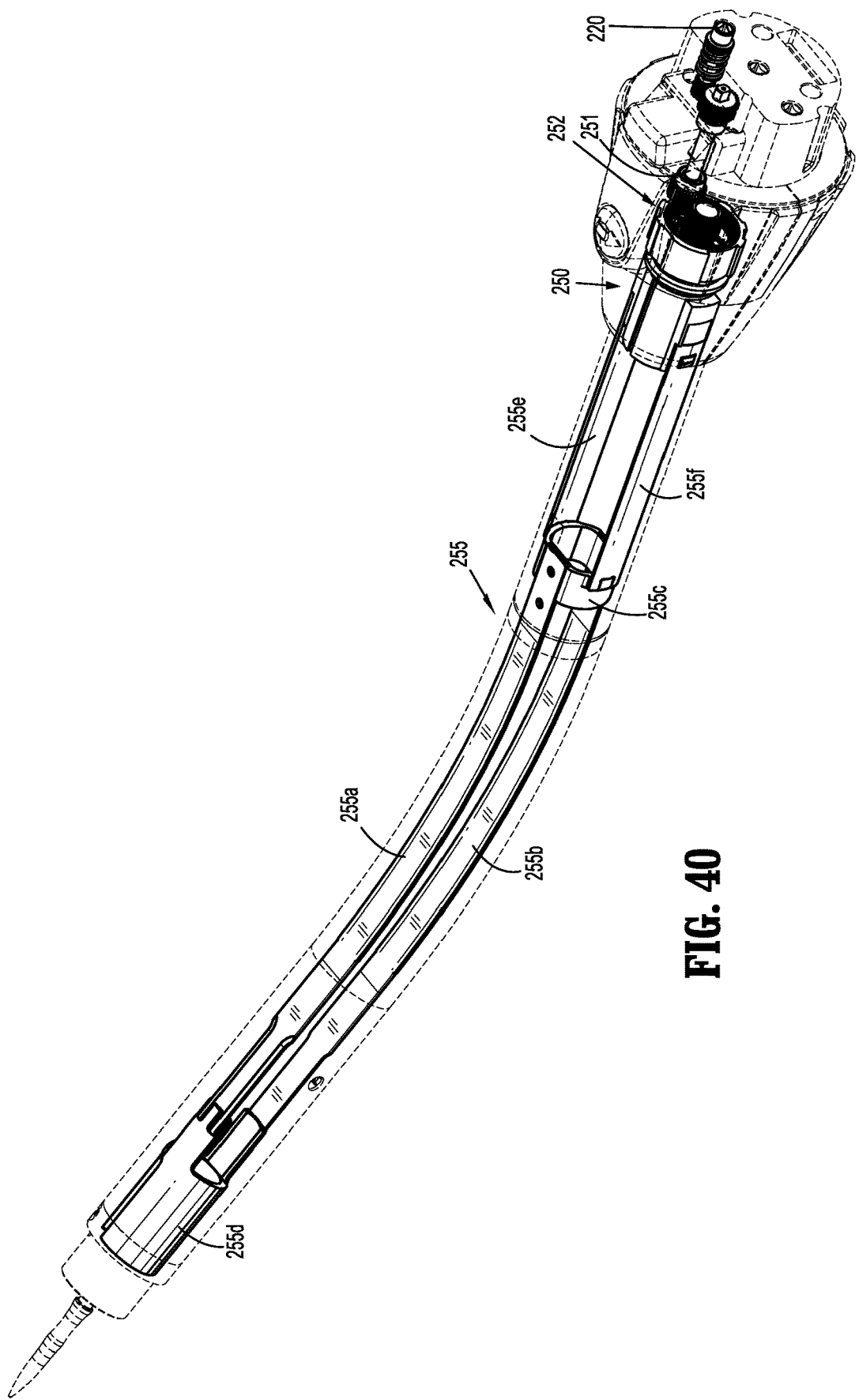
FIG. 40 is a perspective view of the adapter assembly of FIG. 4, shown partially in phantom, illustrating a second force/rotation transmitting/converting assembly thereof.

As shown in FIGS. 6 and 40, the second force/rotation transmitting/converting assembly 250 of adapter assembly 200 includes the second proximal drive shaft 214, as described above, a first coupling shaft 251, a planetary gear set 252, a staple lead screw 253, and a staple driver 254. The second force/rotation transmitting/converting assembly 250 of the adapter assembly 200 also includes an outer flexible band assembly 255 secured to the staple driver 254. The outer flexible band assembly 255 includes first and second flexible bands 255a, 255b laterally spaced and connected at proximal ends thereof to a support ring 255c and at distal ends thereof to a proximal end of a support base 255d. The outer flexible band assembly 255 further includes first and second connection extensions 255e, 255f extending proximally from the support ring 255c that are configured to operably connect the outer flexible band assembly 255 to the staple driver 254. The second force/rotation transmitting/converting assembly 250 functions to fire staples "S" (FIG. 13) of the reload 400 for formation against the anvil assembly 510.

In operation, as the second rotatable proximal drive shaft 214 is rotated due to a rotation of the second connector sleeve 220, as a result of the rotation of the second coupling shaft 124c (FIG. 2) of the handle assembly 100, the first coupling shaft 251 is caused to be rotated, which in turn causes the planetary gear set 252 to rotate. Rotation of the planetary gear set 252 causes contemporaneous rotation of the staple lead screw 253. As the staple lead screw 253 is rotated, the staple driver 254 is caused to be axially translated, which in turn causes the outer flexible band assembly 255 to be axially translated. As the outer flexible band assembly 255 is axially translated, the support base 255d presses against a driver adapter of a staple driver assembly (not shown) of the reload 400 to distally advance a driver and fire staples from a staple cartridge (not shown) of the reload 400 and against anvil assembly 510 for formation of the staples in underlying tissue.

Figure 41:
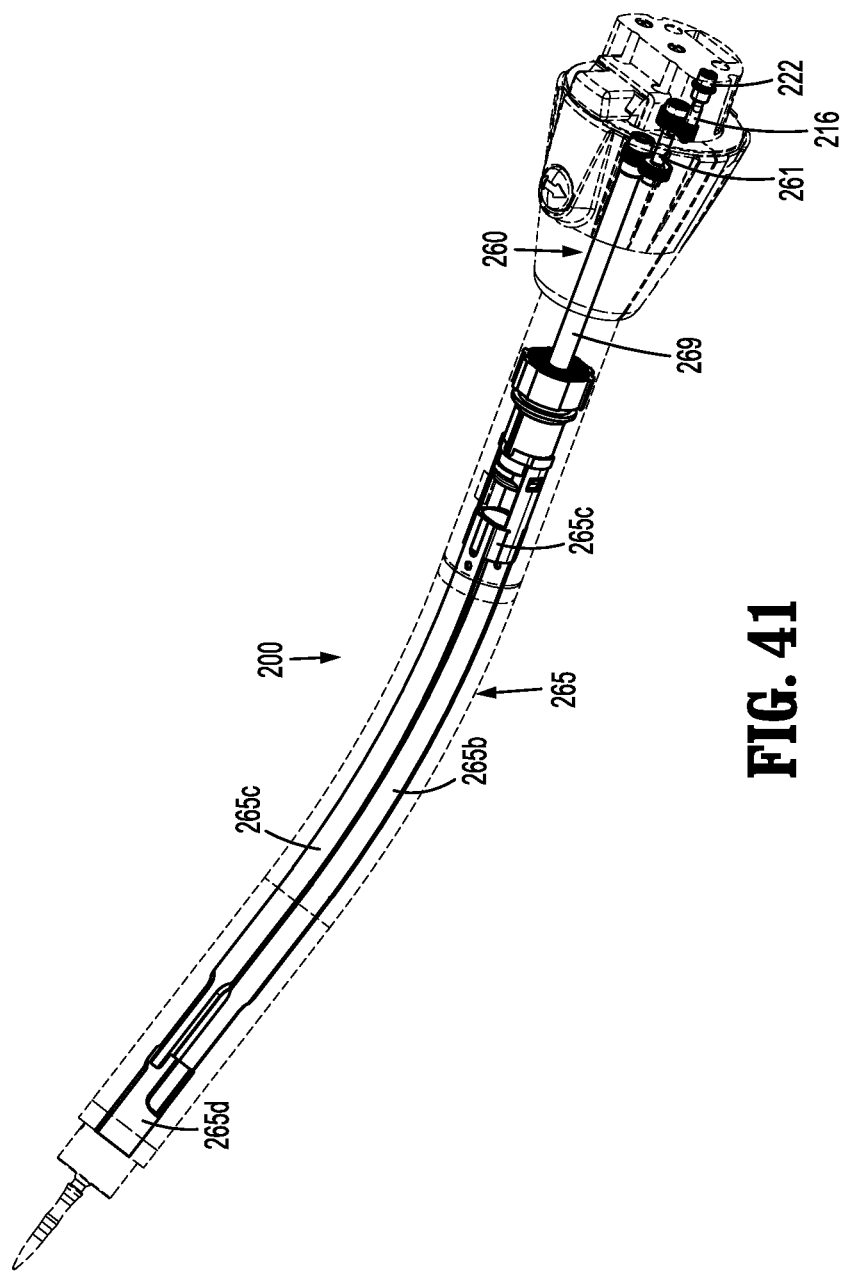
FIG. 41 is a perspective view of the adapter assembly of FIG. 4, shown partially in phantom, illustrating a third force/rotation transmitting/converting assembly thereof.

With reference to FIGS. 6 and 41, the third force/rotation transmitting/converting assembly 260 of the adapter assembly 200 includes the third proximal drive shaft 216, as described above, a second coupling shaft 261, a hollow shaft 269, a planetary gear set 262, a knife lead screw 263, and a knife driver 264. The third force/rotation transmitting/converting assembly 260 of adapter assembly 200 also includes an inner flexible band assembly 265 secured to the knife driver 264. The inner flexible band assembly 265 includes first and second flexible bands 265a, 265b laterally spaced and connected at proximal ends thereof to a support ring 265c and at distal ends thereof to a proximal end of a support base 265d. The third force/rotation transmitting/converting assembly 260 functions to fire an annular knife 444 (FIG. 13) of the reload 400.

In operation, as the third rotatable proximal drive shaft 216 is rotated due to a rotation of the third connector sleeve 222, as a result of the rotation of the third coupling shaft 124b (FIG. 2) of the handle assembly 100, the second coupling shaft 261 is caused to be rotated, which in turn causes the hollow shaft 269 to rotate. Rotation of the hollow shaft 269 results in contemporaneous rotation of the planetary gear set 262, which in turn causes the knife lead screw 263 to rotate. As the knife lead screw 263 is rotated, the knife driver 264 is caused to be axially translated, which in turn causes the inner flexible band assembly 265 to be axially translated. As the inner flexible band assembly 265 is axially translated, the support base 265d presses against a knife carrier (not shown) of the reload 400 to distally advance the knife carrier and fire the an annular knife (not shown) of the reload 400 against the anvil assembly 510 for cutting of tissue clamped in the reload 400.

Persons skilled in the art will understand that the structures specifically described herein and shown in the accompanying figures are non-limiting exemplary embodiments and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. For example, the electrical assemblies of the present disclosure may be configured for use with a plurality of different reloads via a plurality of respective adapter assemblies that are each configured for actuation and manipulation by a powered handle assembly and/or a robotic surgical system. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An adapter assembly for connecting a surgical reload to an electromechanical handle assembly, the adapter assembly comprising:
    an outer tube;
    a trocar assembly releasably securable within a distal end of the outer tube, the trocar assembly including a trocar housing defining a pair of openings therein, wherein the pair of openings are in opposed radially extending relation to one another; and
    a trocar assembly release mechanism configured to releasably secure the trocar assembly within the outer tube, the release mechanism including:
        a release button supported in the outer tube and movable between an extended condition and a depressed condition;
        a spring clip slidably supported in the outer tube and connected to the release button, the spring clip including:
            a backspan connected to the release button; and
            a pair of legs extending from the backspan; and
        a pair of lock cam pins supported within the outer tube, wherein each lock cam pin is secured to a respective leg of the spring clip, and wherein each lock cam pin is selectively receivable within a respective opening of the pair of openings formed in the trocar housing;
    wherein, when the release button is moved from the extended condition to the depressed condition, the spring clip acts on the pair of lock cam pins to withdraw the pair of lock cam pins from the openings of the trocar housing to release the trocar assembly from the outer tube, and
    wherein, when the release button is moved from the depressed condition to the extended condition, the spring clip acts on the pair of lock cam pins to urge the pair of lock cam pins into the openings of the trocar housing to lock the trocar assembly into the outer tube.

2. The adapter assembly of claim 1, wherein the trocar assembly release mechanism further comprises a biasing member supported within the outer tube and acting on the release button to urge the release button to the extended condition.

3. The adapter assembly of claim 1, wherein each lock cam pin includes:
    a lock boss extending from a respective leg of the spring clip; and
    a cam surface configured for engagement by a feature of the adapter assembly to cause the lock cam pin to move outwardly as the release button from the extended condition to the depressed condition.

4. The adapter assembly of claim 3, wherein each lock boss is configured for receipt into the openings of the trocar housing to lock the trocar assembly into the outer tube.

5. The adapter assembly of claim 1, wherein the trocar assembly further includes:
    a trocar member slidably disposed within a lumen of the trocar housing, wherein the trocar member and the trocar housing are keyed to one another to inhibit rotation relative to one another, wherein the trocar member includes a distal end defining a tip and a proximal end defining an internally threaded bore; and
    a drive screw having a threaded distal portion engaged with the threaded bore of the trocar member, and a proximal force receiving feature for receiving rotative forces from the electromechanical handle assembly.

6. The adapter assembly of claim 1, wherein, when the release button is moved from the extended condition to the depressed condition, the cam surfaces of the pair of lock cam pins engage respective camming surfaces of the adapter assembly to withdraw the pair of lock cam pins from the openings of the trocar housing to release the trocar assembly from the outer tube.

7. The adapter assembly of claim 6, wherein, during movement of the release button from the extended condition to the depressed condition, the pair of legs of the spring clip are splayed outwardly, whereby a spring bias is created in the spring clip.

8. The adapter assembly of claim 7, wherein the spring bias of the spring clip urges the pair of legs towards one another to move the pair of lock cam pins towards one another.

9. The adapter assembly of claim 7, wherein the spring bias of the spring clip urges the release button from the depressed condition to the extended condition.

10. An adapter assembly for connecting a surgical reload to an electromechanical handle assembly, the adapter assembly comprising:
    an outer tube;
    a trocar assembly releasably securable within a distal end of the outer tube, the trocar assembly including a trocar housing defining a pair of openings therein, wherein the pair of openings are in opposed radially extending relation to one another; and a trocar assembly release mechanism configured to releasably secure the trocar assembly within the outer tube, the release mechanism including:
- a release button supported in the outer tube and movable between an extended condition and a depressed condition;
- a spring clip slidably supported in the outer tube and connected to the release button, wherein the spring clip of the trocar assembly release mechanism creates a spring bias when the release button is moved from the extended condition to the depressed condition, the spring clip including:
  - a backspan connected to the release button; and
  - a pair of legs extending from the backspan; and
- a pair of lock cam pins supported within the outer tube, wherein each lock cam pin is secured to a respective leg of the spring clip, and wherein each lock cam pin is selectively receivable within a respective opening of the pair of openings formed in the trocar housing;
wherein, when the release button is moved from the extended condition to the depressed condition, the spring clip acts on the pair of lock cam pins to withdraw the pair of lock cam pins from the openings of the trocar housing to release the trocar assembly from the outer tube.

11. The adapter assembly of claim 10, wherein movement of the release button from the extended condition to the depressed condition causes the pair of legs of the spring clip to splay outwardly.

12. The adapter assembly of claim 11, wherein when the release button is in the extended condition, the pair of legs of the spring clip biases the pair of lock cam pins towards one another.

13. The adapter assembly of claim 10, wherein the trocar assembly release mechanism further comprises a biasing member supported within the outer tube and acting on the release button to urge the release button to the extended condition.

14. The adapter assembly of claim 10, wherein the trocar assembly further includes:
- a trocar member slidably disposed within a lumen of the trocar housing, wherein the trocar member and the trocar housing are keyed to one another to inhibit rotation relative to one another, wherein the trocar member includes a distal end defining a tip and a proximal end defining an internally threaded bore; and
- a drive screw having a threaded distal portion engaged with the threaded bore of the trocar member, and a proximal force receiving feature for receiving rotative forces from the electromechanical handle assembly.

15. An adapter assembly for connecting a surgical reload to an electromechanical handle assembly, the adapter assembly comprising:
- an outer tube;
- a trocar assembly releasably securable within a distal end of the outer tube, the trocar assembly including a trocar housing defining a pair of openings therein, wherein the pair of openings are in opposed radially extending relation to one another; and
- a trocar assembly release mechanism configured to releasably secure the trocar assembly within the outer tube, the release mechanism including:
  - a release button supported in the outer tube and movable between an extended condition and a depressed condition;
  - a spring clip slidably supported in the outer tube and connected to the release button, the spring clip including:
    - a backspan connected to the release button; and
    - a pair of legs extending from the backspan; and
  - a pair of lock cam pins supported within the outer tube, wherein each lock cam pin is secured to a respective leg of the spring clip, and wherein each lock cam pin is selectively receivable within a respective opening of the pair of openings formed in the trocar housing, wherein each lock cam pin includes:
    - a lock boss extending from a respective leg of the spring clip; and
    - a cam surface configured for engagement by a feature of the adapter assembly to cause the lock cam pins to move outwardly as the release button moves from the extended condition to the depressed condition, wherein each cam surface is defined by a pair of camming surfaces respectively associated with the cam surface of each of the lock cam pins,
  wherein, when the release button is moved from the extended condition to the depressed condition, the spring clip acts on the pair of lock cam pins to withdraw the pair of lock cam pins from the openings of the trocar housing to release the trocar assembly from the outer tube.

16. The adapter assembly of claim 15, wherein, when the release button is moved from the extended condition to the depressed condition, the cam surfaces of the lock cam pins engage respective camming surfaces of the adapter assembly to withdraw the pair of lock cam pins from the openings of the trocar housing to release the trocar assembly from the outer tube.

17. The adapter assembly of claim 16, wherein, during movement of the release button from the extended condition to the depressed condition, the pair of legs of the spring clip are splayed outwardly, whereby a spring bias is created in the spring clip.

18. The adapter assembly of claim 17, wherein the spring bias of the spring clip urges the pair of legs towards one another to move the pair of lock cam pins towards one another.

19. The adapter assembly of claim 17, wherein the spring bias of the spring clip urges the release button from the depressed condition to the extended condition.

20. The adapter assembly of claim 15, wherein the trocar assembly release mechanism further comprises a biasing member supported within the outer tube and acting on the release button to urge the release button to the extended condition.

21. The adapter assembly of claim 15, wherein the trocar assembly further includes:
- a trocar member slidably disposed within a lumen of the trocar housing, wherein the trocar member and the trocar housing are keyed to one another to inhibit rotation relative to one another, wherein the trocar member includes a distal end defining a tip and a proximal end defining an internally threaded bore; and
- a drive screw having a threaded distal portion engaged with the threaded bore of the trocar member, and a proximal force receiving feature for receiving rotative forces from the electromechanical handle assembly.

22. The adapter assembly of claim 15, wherein the trocar assembly release mechanism further comprises a biasing member supported within the outer tube and acting on the release button to urge the release button to the extended condition.

\* \* \* \* \*